United States Patent
Nassif

(10) Patent No.: US 12,268,880 B2
(45) Date of Patent: Apr. 8, 2025

(54) LOW ENERGY IMPLANTABLE DEVICES AND METHODS OF USE

(71) Applicant: Axonics, Inc., Irvine, CA (US)

(72) Inventor: Rabih Nassif, Santa Ana, CA (US)

(73) Assignee: Axonics, Inc., Irvine, CA (US)

( * ) Notice: Subject to any disclaimer, the term of this patent is extended or adjusted under 35 U.S.C. 154(b) by 0 days.

(21) Appl. No.: 17/986,660

(22) Filed: Nov. 14, 2022

(65) Prior Publication Data
US 2023/0080703 A1    Mar. 16, 2023

Related U.S. Application Data

(63) Continuation of application No. 16/878,505, filed on May 19, 2020, now abandoned.

(60) Provisional application No. 62/852,255, filed on May 23, 2019.

(51) Int. Cl.
*A61N 1/36* (2006.01)

(52) U.S. Cl.
CPC ..... *A61N 1/36192* (2013.01); *A61N 1/36007* (2013.01); *A61N 1/36125* (2013.01); *A61N 1/36175* (2013.01)

(58) Field of Classification Search
CPC ............ A61N 1/36192; A61N 1/36007; A61N 1/36125; A61N 1/36175; A61N 1/36146; A61N 1/3614
See application file for complete search history.

(56) References Cited

U.S. PATENT DOCUMENTS

| | | | |
|---|---|---|---|
| 2005/0245994 A1* | 11/2005 | Varrichio | A61N 1/14 607/30 |
| 2010/0023070 A1* | 1/2010 | Moffitt | A61N 1/36071 607/2 |
| 2011/0077698 A1* | 3/2011 | Tsampazis | A61N 1/36038 607/2 |
| 2011/0106214 A1 | 5/2011 | Carbunaru et al. | |
| 2012/0116483 A1* | 5/2012 | Yonezawa | A61N 1/36125 607/2 |
| 2013/0073008 A1* | 3/2013 | Ternes | A61N 1/3614 607/62 |

(Continued)

OTHER PUBLICATIONS

International Search Report and Written Opinion dated Sep. 25, 2020 issued by the International Searching Authority in related International Patent Application No. PCT/US2020/033628; filed May 19, 2020.

*Primary Examiner* — Ankit D Tejani
*Assistant Examiner* — Joshua Brendon Solomon
(74) *Attorney, Agent, or Firm* — Gordon Rees Scully Mansukhani, LLP

(57) ABSTRACT

An implantable neurostimulator for delivering one or more stimulation pulses to a target region within a patient's body. The implantable neurostimulator including a housing and an energy storage feature. There is also a lead coupled to the hermetic housing and a plurality of electrodes located proximate to a distal end of the lead. The neurostimulator includes stimulation circuitry that includes an adjustable resistance element. A voltage of the electric signal derived from the energy storage feature and a resistance of the adjustable resistance element are both adjusted based on a measurement of a value indicative of a tissue impedance of the target region to provide a desired value of a stimulation current for the one or more stimulation pulses.

16 Claims, 18 Drawing Sheets

(56) References Cited

U.S. PATENT DOCUMENTS

| | | |
|---|---|---|
| 2014/0214131 A1 | 7/2014 | Bradley et al. |
| 2014/0303691 A1* | 10/2014 | McDermott ....... A61N 1/36175 607/72 |
| 2016/0008602 A1* | 1/2016 | Perryman .......... A61N 1/37223 607/61 |
| 2016/0121123 A1 | 5/2016 | Jiang et al. |
| 2017/0001023 A1 | 1/2017 | Peterson et al. |
| 2017/0120061 A1 | 5/2017 | Nassif et al. |
| 2017/0157414 A1* | 6/2017 | Anderson .............. A61N 1/371 |
| 2017/0216609 A1 | 8/2017 | Nassif et al. |
| 2018/0071512 A1* | 3/2018 | Feldman ................ A61N 1/025 |
| 2018/0140831 A1* | 5/2018 | Feldman ................ A61N 1/375 |
| 2018/0333581 A1 | 11/2018 | Nassif |
| 2019/0001139 A1* | 1/2019 | Mishra ............... A61N 1/36075 |
| 2019/0009098 A1 | 1/2019 | Jiang et al. |
| 2019/0255333 A1* | 8/2019 | Baru ................. A61N 1/36153 |

\* cited by examiner

LOW ENERGY IMPLANTABLE DEVICES AND METHODS OF USE

CROSS-REFERENCES TO RELATED APPLICATIONS

This application claims the benefit of U.S. Provisional Application No. 62/852,255, filed on May 23, 2019, and entitled "Low Energy Implantable Devices And Methods Of Use," the entirety of which is hereby incorporated by reference herein.

FIELD

The present invention relates to neurostimulation treatment systems and associated devices, as well as methods of treatment, implantation and configuration of such treatment systems.

BACKGROUND

Treatments with implantable neurostimulation systems have become increasingly common in recent years. While such systems have shown promise in treating a number of conditions, effectiveness of treatment may vary considerably between patients. A number of factors may lead to the very different outcomes that patients experience, and viability of treatment can be difficult to determine before implantation. For example, stimulation systems often make use of an array of electrodes to treat one or more target nerve structures. The electrodes are often mounted together on a multi-electrode lead, and the lead implanted in tissue of the patient at a position that is intended to result in electrical coupling of the electrode to the target nerve structure, typically with at least a portion of the coupling being provided via intermediate tissues. Other approaches may also be employed, for example, with one or more electrodes attached to the skin overlying the target nerve structures, implanted in cuffs around a target nerve, or the like. Regardless, the physician will typically seek to establish an appropriate treatment protocol by varying the electrical stimulation that is applied to the electrodes.

Current stimulation electrode placement/implantation techniques and known treatment setting techniques suffer from significant disadvantages. The nerve tissue structures of different patients can be quite different, with the locations and branching of nerves that perform specific functions and/or enervate specific organs being challenging to accurately predict or identify. The electrical properties of the tissue structures surrounding a target nerve structure may also be quite different among different patients, and the neural response to stimulation may be markedly dissimilar, with an electrical stimulation pulse pattern, frequency, and/or voltage that is effective to affect a body function for one patent may impose significant pain on, or have limited effect for, another patient. Even in patients where implantation of a neurostimulation system provides effective treatment, frequent adjustments and changes to the stimulation protocol are often required before a suitable treatment program can be determined, often involving repeated office visits and significant discomfort for the patient before efficacy is achieved. While a number of complex and sophisticated lead structures and stimulation setting protocols have been implemented to seek to overcome these challenges, the variability in lead placement results, the clinician time to establish suitable stimulation signals, and the discomfort (and in cases the significant pain) that is imposed on the patient remain less than ideal. In addition, the lifetime and battery life of such devices is relatively short, such that implanted systems are routinely replaced every few years, which requires additional surgeries, patient discomfort, and significant costs to healthcare systems.

Furthermore, current stimulation systems rely on recharging of energy storage features such as batteries that are used in generating stimulation of the patient's tissue. Many of the recharging systems utilize wireless power transfer techniques to transcutaneously provide power for recharging the energy storage features. Such wireless power transfer techniques frequently utilize coupling between a charging device external to the patient and a stimulator implanted within the patient. The effectiveness of this coupling can vary based on: the relative position of the charging device with respect to the stimulator; the orientation of the charging device with respect to the stimulator; and/or the distance separating the charging device and the stimulator.

The tremendous benefits of these neural stimulation therapies have not yet been fully realized. Therefore, it is desirable to provide improved neurostimulation methods, systems and devices, as well as methods for implanting and configuring such neurostimulation systems for a particular patient or condition being treated. It would be particularly helpful to provide such systems and methods so as to improve ease of coupling between the charging device and the implanted stimulator.

BRIEF SUMMARY

Some aspects of the present disclosure relate to low-power consumption implantable pulse generators. Implantable pulse generators can deliver energy to a patient in the form of one or several stimulation pulses. This energy can be stored in an energy storage feature such as one or several batteries and/or capacitors. Some such implantable devices can be rechargeable to allow the recharging of these energy storage features, whereas some implantable devices are non-rechargeable. In rechargeable devices, depletion of the energy in the energy storage features can necessitate recharging of the energy storage features before further treatment can be delivered, and in non-rechargeable devices, depletion of the energy in the energy storage features can necessitate a surgical intervention, such as, for example replacement of the implantable device or replacement of the energy storage features of the implantable device, before further treatments can be delivered.

While the inconvenience caused by the depletion of the energy storage features can, in some instances, be mitigated by increasing the size or number of the energy storage features, such increasing of the size or number of the energy storage features can be detrimental. In some aspects of the present disclosure, the implantable device includes stimulation circuitry that decreases power consumption. This decrease in power consumption can be accomplished via stimulation circuitry that control the sourcing and/or sinking of current via modulation of the voltage of a power source and/or modification of a resistance of one or several resistors. In some embodiments, these one or several resistors can be one or several adjustable resistance elements. Through this diminished power consumption of the implantable device, therapy can be provided with less frequently depletion of the energy storage features of the implantable device.

One aspect of the present disclosure relates to an implantable neurostimulator for delivering one or more electrical pulses to a target region within a patient's body. The implantable neurostimulator can include a hermetic housing made of a biocompatible material, an energy storage feature that can power the implantable neurostimulator, and at least one lead coupled to the hermetic housing. The lead can include a plurality of electrodes located proximate to a distal end of the at least one lead. The implantable neurostimulator can include stimulation circuitry including a first circuit selectively coupleable to a first one of the plurality of electrodes and a second circuit selectively coupleable to a second one of the plurality of electrodes. The first circuit can include an adjustable resistance element having a first terminal and a second terminal. A first switch can be coupled to the first terminal of the adjustable resistance element, and the first switch can be selectively coupleable with a stimulation-voltage node and with a ground node. The first circuit can include a second switch selectively coupling the first one of the plurality of electrodes to one of: the second terminal of the adjustable resistance element; and the stimulation-voltage node.

In some embodiments, the adjustable resistance element can be a variable resistor that can be at least one of: a potentiometer; or a rheostat. In some embodiments, wherein the adjustable resistance element can be at least one of: a digital resistor, or a bank of resistors switchably connectable to generate a desired combined resistance. In some embodiments, the implantable neurostimulator can further include a processor that can operate according to stored instructions to control the first and second switches to generate a stimulation pulse.

In some embodiments, the second circuit can include: a second adjustable resistance element having a first terminal and a second terminal, a third switch coupled to the first terminal of the second adjustable resistance element, and a fourth switch selectively coupling the second one of the plurality of electrodes to one of: the second terminal of the second adjustable resistance element; and the stimulation-voltage node. In some embodiments, the third switch can be selectively coupleable with the stimulation-voltage node and the ground node. In some embodiments, the processor can further operate according to stored instructions to control the third and fourth switches in connection with the control of the first and second switches to generate the stimulation pulse.

In some embodiments, the neurostimulator can further include a first capacitor located between the second switch and the first one of the plurality of electrodes, and a second capacitor located between the fourth switch and the second one of the plurality of electrodes. In some embodiments, the processor can operate according to stored instructions to control the first, second, third, and fourth switches to selectively charge and discharge at least one of the first and second capacitors.

In some embodiments, the processor can operate according to stored instructions to adjust the resistance of at least one of the adjustable resistance element and the second adjustable resistance element to control a rate of at least one of the charging and the discharging of the at least one of the first and second capacitors. In some embodiments, the processor can operate according to stored instructions to repeatedly determine an impedance of tissue in the target region of the patient's body. In some embodiments, the processor can operate according to stored instructions to repeatedly determine the impedance of tissue in the target region of the patient's body based on a current through the adjustable resistance element and a voltage of the stimulation voltage node.

In some embodiments, the processor can operate according to stored instructions to control the stimulation circuitry to deliver a stimulation pulse having a desired amplitude. In some embodiments, controlling the stimulation circuitry to deliver a stimulation pulse having a desired amplitude includes controlling the stimulation circuitry to deliver a plurality of stimulation pulses with progressively increasing amplitudes until the stimulation pulse having the desired amplitude is delivered.

One aspect of the present disclosure relates to a method of delivering stimulation to a target tissue of a patient. The method includes coupling a first electrode of a lead having a plurality of electrodes to a first circuit of a stimulation circuitry an implantable pulse generator, coupling a second electrode of the lead to a second circuit of the stimulation circuitry of the implantable pulse generator, delivering a first phase of a stimulation pulse via implementing of a first switch configuration in the first circuit and in the second circuit of the stimulation circuitry, implementing a second switch configuration corresponding to an interphase delay in the first circuit and in the second circuit, delivering a second phase of the stimulation pulse via implementing of a third switch configuration, and adjusting a resistance of the adjustable resistance element in the first circuit to control a current of the second phase of the stimulation pulse.

In some embodiments, the third switch configuration couples both the first circuit and the second circuit to a node. In some embodiments, the first circuit includes: an adjustable resistance element having a first terminal and a second terminal; a first switch coupled to the first terminal of the adjustable resistance element, the first switch selectively coupleable with a stimulation-voltage node and a ground node, and a second switch selectively coupling the a first one of the plurality of electrodes to one of: the second terminal of the adjustable resistance element; and the stimulation-voltage node. In some embodiments, the first switch configuration couples the first switch of the first circuit to a ground node and the second circuit to a stimulation voltage node.

In some embodiments, the method includes measuring an impedance of the target tissue prior to delivering the second phase of the stimulation pulse. In some embodiments, the adjustable resistance element is adjusted according to the measured impedance of the target tissue. In some embodiments, the method includes controlling a current of the first phase of the stimulation pulse via at least one of: controlling a voltage of the stimulation voltage node; or adjusting the resistance of the adjustable resistance element. In some embodiments, a second direction of the current of the stimulation pulse in the second phase is in a direction opposite to a first direction of the current of the stimulation pulse in the first phase.

In some embodiments, the adjustable resistance element can be made from a plurality of resistors switchably connectable to generate a desired combined resistance. In some embodiments, adjusting the resistance of the adjustable resistance element can include changing a switch configuration of at least one of the plurality of resistors. In some embodiments, the node can be a common voltage node. In some embodiments, the node can be the stimulation voltage node.

In some embodiments, the voltage of the stimulation voltage node is set to a first voltage during the first phase and to a second voltage during the second phase. In some embodiments, the second switch configuration includes opening of at least one switch of the stimulation circuitry. In some embodiments, a charge of the first phase of the stimulation pulse is equal to a charge of the second phase of the stimulation pulse.

One aspect of the present disclosure relates to a method of delivering stimulation to a target tissue of a patient with an implantable pulse generator. The method includes determining a desired value of a current of desired stimulation pulse, delivering a first stimulation pulse having a first current, which current of the first stimulation pulse has a value less than the desired value of the current of the desired stimulation pulse, measuring a first impedance of the target tissue of the patient at the first current of the first stimulation pulse; and delivering a second stimulation pulse having a second current set based on the first impedance.

In some embodiments, the second current is equal to the desired value of the current of the desired stimulation pulse. In some embodiments, the second current is less than the desired value of the current of the desired stimulation pulse. In some embodiments, the method includes measuring a second impedance of the target tissue of the patient at the second current, and delivering a third stimulation pulse having a third current set based on the second impedance. In some embodiments, the third current is greater than the second current, and the second current is greater than the first current.

In some embodiments, each of the first stimulation pulse, the second stimulation pulse, and the third stimulation pulse include a first pulse delivery phase having a first phase current and a second pulse delivery phase having a second phase current. In some embodiments, the first phase current is controlled via at least one of: control of a voltage of a node selectably coupleable to the target tissue of the patient via stimulation circuitry of the implantable pulse generator, or control of a resistance of an adjustable resistance element of the stimulation circuitry. In some embodiments, the second phase current is controlled via control of the resistance of the adjustable resistance element of the stimulation circuitry. In some embodiments, the third current is equal to the desired value of the current of the desired stimulation pulse.

One aspect of the present disclosure relates to a method of delivering stimulation to a target tissue of a patient with an implantable pulse generator. The method includes determining a desired value of a current of a desired stimulation pulse, iteratively: delivering a test stimulation pulse with stimulation circuitry having a setting to deliver a current less than the desired value of the current of the desired stimulation pulse, measuring an impedance of the target tissue of the patient during delivery of the test stimulation pulse, and until the current of the test stimulation pulse approximately matches the desired value of the current of the desired stimulation pulse, updating the setting of the stimulation circuitry to deliver an increased stimulation current.

In some embodiments, each of the stimulation pulses includes a first pulse delivery phase having a first phase current and a second pulse delivery phase having a second phase current. In some embodiments, a second direction of the current of the stimulation pulse in the second phase is in a direction opposite to a first direction of the current of the stimulation pulse in the first phase. In some embodiments, the current of the test stimulation pulse approximately matches the desired value of the current of the desired stimulation pulse when at least one of: the first phase current; or the second phase current approximately matches the desired value of the current of the desired stimulation pulse.

In some embodiments, the at least one of: the first phase current; or the second phase current approximately matches the desired value of the current of the desired stimulation pulse when the current of the at least one of: the first phase current; or the second phase current is within predetermined range about the desired value of the current of the desired stimulation pulse. In some embodiments, the method includes repeatedly delivering stimulation pulses with stimulation circuitry having the setting to match the setting of the test stimulation pulse approximately matching the desired value of the current of the desired stimulation pulse, determining a change in the impedance of the target tissue, and adjusting the setting of the stimulation circuitry based on the changed impedance of the target tissue. In some embodiments, updating the setting of the stimulation circuitry includes updating a resistance of an adjustable resistance element. In some embodiments, updating the setting of the stimulation circuitry includes updating the voltage of a voltage node selectively coupled to the stimulation circuitry.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

DETAILED DESCRIPTION

Figure 1:
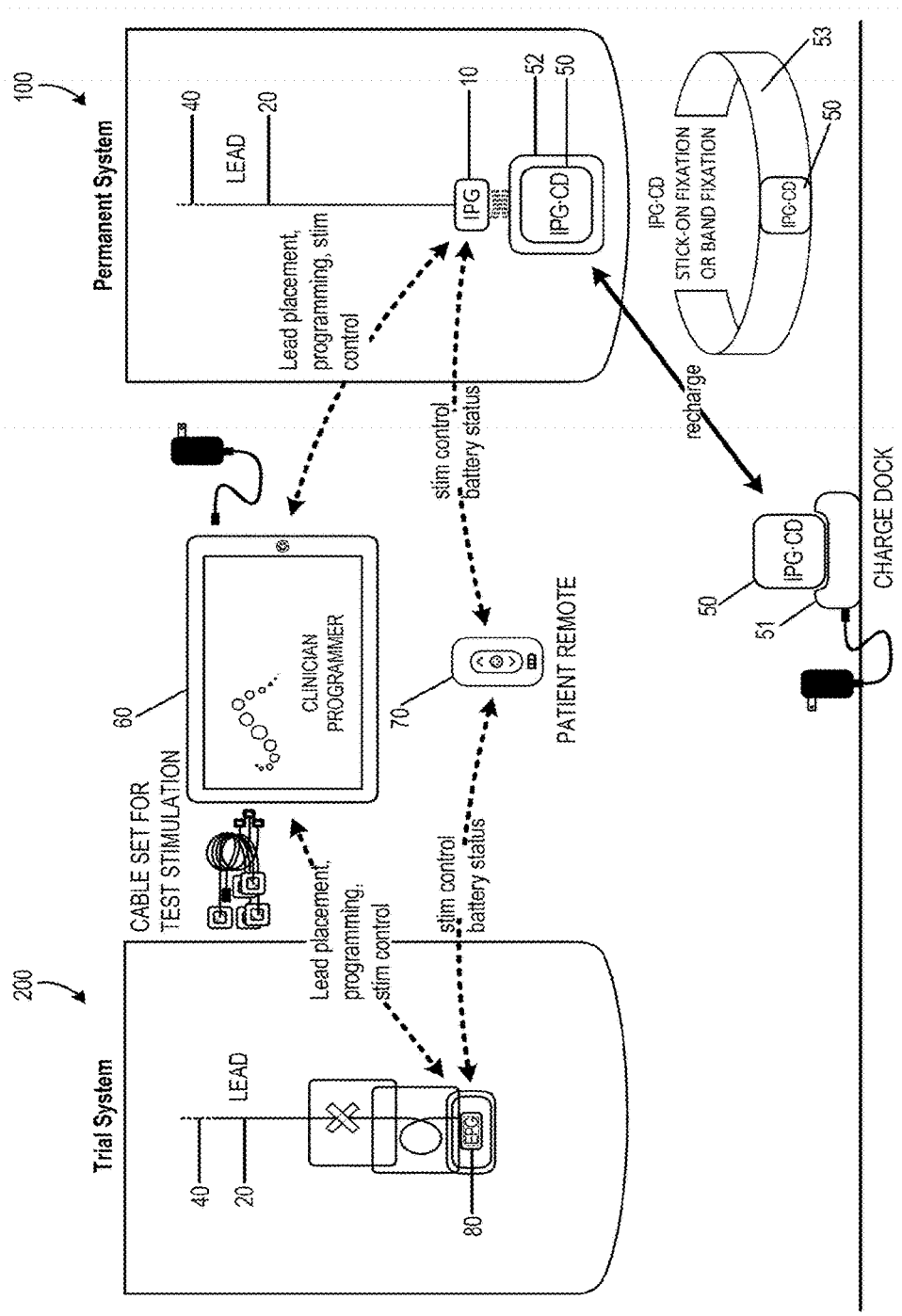
FIG. 1 schematically illustrates a nerve stimulation system, which includes a clinician programmer and a patient remote used in positioning and/or programming of both a trial neurostimulation system and a permanently implanted neurostimulation system, in accordance with aspects of the invention.

The present invention relates to neurostimulation treatment systems and associated devices, as well as methods of treatment, implantation/placement and configuration of such treatment systems. In one particular embodiment, the invention relates to sacral nerve stimulation treatment systems configured to treat overactive bladder ("OAB") and relieve symptoms of bladder related dysfunction. It will be appreciated, however, that the present invention may also be utilized for any variety of neuromodulation uses, such as fecal dysfunction, the treatment of pain or other indications, such as movement or affective disorders, as will be appreciated by one of skill in the art.

I. Neurostimulation Indications

Neurostimulation (or neuromodulation as may be used interchangeably hereunder) treatment systems, such as any of those described herein, can be used to treat a variety of ailments and associated symptoms, such as acute pain disorders, movement disorders, affective disorders, as well as bladder related dysfunction. Examples of pain disorders that may be treated by neurostimulation include failed back surgery syndrome, reflex sympathetic dystrophy or complex regional pain syndrome, causalgia, arachnoiditis, and peripheral neuropathy. Movement orders include muscle paralysis, tremor, dystonia and Parkinson's disease. Affective disorders include depressions, obsessive-compulsive disorder, cluster headache, Tourette syndrome and certain types of chronic pain. Bladder related dysfunctions include but are not limited to OAB, urge incontinence, urgency-frequency, and urinary retention. OAB can include urge incontinence and urgency-frequency alone or in combination. Urge incontinence is the involuntary loss or urine associated with a sudden, strong desire to void (urgency). Urgency-frequency is the frequent, often uncontrollable urges to urinate (urgency) that often result in voiding in very small amounts (frequency). Urinary retention is the inability to empty the bladder. Neurostimulation treatments can be configured to address a particular condition by effecting neurostimulation of targeted nerve tissues relating to the sensory and/or motor control associated with that condition or associated symptom.

In one aspect, the methods and systems described herein are particularly suited for treatment of urinary and fecal dysfunctions. These conditions have been historically underrecognized and significantly underserved by the medical community. OAB is one of the most common urinary dysfunctions. It is a complex condition characterized by the presence of bothersome urinary symptoms, including urgency, frequency, nocturia and urge incontinence. It is estimated that about 33 million Americans suffer from OAB. Of the adult population, about 30% of all men and 40% of all women live with OAB symptoms.

OAB symptoms can have a significant negative impact on the psychosocial functioning and the quality of life of patients. People with OAB often restrict activities and/or develop coping strategies. Furthermore, OAB imposes a significant financial burden on individuals, their families, and healthcare organizations. The prevalence of co-morbid conditions is also significantly higher for patients with OAB than in the general population. Co-morbidities may include falls and fractures, urinary tract infections, skin infections, vulvovaginitis, cardiovascular, and central nervous system pathologies. Chronic constipation, fecal incontinence, and overlapping chronic constipation occur more frequently in patients with OAB.

Conventional treatments of OAB generally include lifestyle modifications as a first course of action. Lifestyle modifications include eliminating bladder irritants (such as caffeine) from the diet, managing fluid intake, reducing weight, stopping smoking, and managing bowel regularity. Behavioral modifications include changing voiding habits (such as bladder training and delayed voiding), training pelvic floor muscles to improve strength and control of urethral sphincter, biofeedback and techniques for urge suppression. Medications are considered a second-line treatment for OAB. These include anti-cholinergic medications (oral, transdermal patch, and gel) and oral beta-3 adrenergic agonists. However, anti-cholinergics are frequently associated with bothersome, systemic side effects including dry mouth, constipation, urinary retention, blurred vision, somnolence, and confusion. Studies have found that more than 50% of patients stop using anti-cholinergic medications within 90 days due to a lack of benefit, adverse events, or cost.

When these approaches are unsuccessful, third-line treatment options suggested by the American Urological Association include intradetrusor (bladder smooth muscle) injections of Botulinum Toxin (BoNT-A), Percutaneous Tibial Nerve Stimulation (PTNS) and Sacral Nerve Stimulation (SNM). BoNT-A (Botox®) is administered via a series of intradetrusor injections under cystoscopic guidance, but repeat injections of Botox are generally required every 4 to 12 months to maintain effect and Botox may undesirably result in urinary retention. A number of randomized controlled studies have shown some efficacy of BoNT-A in OAB patients, but long-term safety and effectiveness of BoNT-A for OAB is largely unknown.

Alternative treatment methods, typically considered when the above approaches prove ineffective, is neurostimulation of nerves relating to the urinary system. Such neurostimulation methods include PTNS and SNM. PTNS therapy consists of weekly, 30-minute sessions over a period of 12 weeks, each session using electrical stimulation that is delivered from a hand-held stimulator to the sacral plexus via the tibial nerve. For patients who respond well and continue treatment, ongoing sessions, typically every 3-4 weeks, are needed to maintain symptom reduction. There is potential for declining efficacy if patients fail to adhere to the treatment schedule. Efficacy of PTNS has been demonstrated in a few randomized-controlled studies; however, long-term safety and effectiveness of PTNS are relatively unknown at this time.

II. Sacral Neuromodulation

SNM is an established therapy that provides a safe, effective, reversible, and long-lasting treatment option for the management of urge incontinence, urgency-frequency, and non-obstructive urinary retention. SNM therapy involves the use of mild electrical pulses to stimulate the sacral nerves located in the lower back. Electrodes are placed next to a sacral nerve, usually at the S3 level, by inserting the electrode leads into the corresponding foramen of the sacrum. The electrodes are inserted subcutaneously and are subsequently attached to an implantable pulse generator (IPG), also referred to herein as an "implantable neurostimulator" or a "neurostimulator." The safety and effectiveness of SNM for the treatment of OAB, including durability at five years for both urge incontinence and urgency-frequency patients, are supported by multiple studies and are well-documented. SNM has also been approved to treat chronic fecal incontinence in patients who have failed or are not candidates for more conservative treatments.

A. Implantation of Sacral Neuromodulation System

Currently, SNM qualification has a trial phase, and is followed if successful by a permanent implant. The trial phase is a test stimulation period where the patient is allowed to evaluate whether the therapy is effective. Typically, there are two techniques that are utilized to perform the test stimulation. The first is an office-based procedure termed the Percutaneous Nerve Evaluation (PNE) and the other is a staged trial.

In the PNE, a foramen needle is typically used first to identify the optimal stimulation location, usually at the S3 level, and to evaluate the integrity of the sacral nerves. Motor and sensory responses are used to verify correct needle placement, as described in Table 1 below. A temporary stimulation lead (a unipolar electrode) is then placed near the sacral nerve under local anesthesia. This procedure can be performed in an office setting without fluoroscopy. The temporary lead is then connected to an external pulse generator (EPG) taped onto the skin of the patient during the trial phase. The stimulation level can be adjusted to provide an optimal comfort level for the particular patient. The patient will monitor his or her voiding for 3 to 7 days to see if there is any symptom improvement. The advantage of the PNE is that it is an incision free procedure that can be performed in the physician's office using local anesthesia. The disadvantage is that the temporary lead is not securely anchored in place and has the propensity to migrate away from the nerve with physical activity and thereby cause failure of the therapy. If a patient fails this trial test, the physician may still recommend the staged trial as described below. If the PNE trial is positive, the temporary trial lead is removed and a permanent quadri-polar tined lead is implanted along with an IPG under general anesthesia.

Figure 3A:
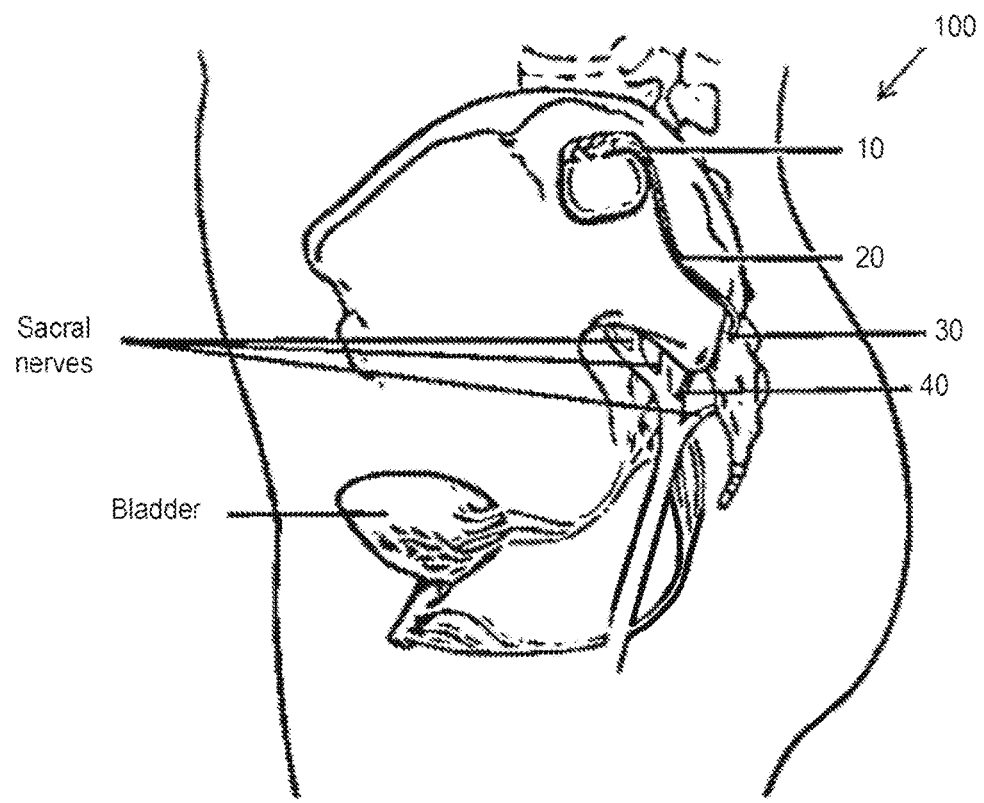
FIG. 3A shows an example of a fully implanted neurostimulation system in accordance with aspects of the invention.

A staged trial involves the implantation of the permanent quadri-polar tined stimulation lead into the patient from the start. It also requires the use of a foramen needle to identify the nerve and optimal stimulation location. The lead is implanted near the S3 sacral nerve and is connected to an EPG via a lead extension. This procedure is performed under fluoroscopic guidance in an operating room and under local or general anesthesia. The EPG is adjusted to provide an optimal comfort level for the patient and the patient monitors his or her voiding for up to two weeks. If the patient obtains meaningful symptom improvement, he or she is considered a suitable candidate for permanent implantation of the IPG under general anesthesia, typically in the upper buttock area, as shown in FIGS. 1 and 3A.

TABLE 1

Motor and Sensory Responses of SNM at Different Sacral Nerve Roots

| | Nerve Innervation | Response | | |
|---|---|---|---|---|
| | | Pelvic Floor | Foot/calf/leg | Sensation |
| S2 | Primary somatic contributor of pudendal nerve for external sphincter, leg, foot | "clamp"* of anal sphincter" | Leg/hip rotation, plantar flexion of entire foot, contraction of calf | Contraction of base of penis, vagina |
| S3 | Virtually all pelvic autonomic functions and striated muscle (levator ani) | "bellows"** of perineum | Plantar flexion of great toe, occasionally other toes | Pulling in rectum, extending forward to scrotum or labia |
| S4 | Pelvic autonomic and somatic No leg or foot | "bellows"** | No lower extremity motor stimulation | Pulling in rectum only |

*Clamp contraction of anal sphincter and, in males, retraction of base of penis. Move buttocks aside and look for anterior/posterior shortening of the perineal structures.
**Bellows: sitting and dropping of pelvic floor. Look for deepening and flattening of buttock grove.

In regard to measuring outcomes for SNM treatment of voiding dysfunction, the voiding dysfunction indications (e.g., urge incontinence, urgency-frequency, and non-obstructive urinary retention) are evaluated by unique primary voiding diary variables. The therapy outcomes are measured using these same variables. SNM therapy is considered successful if a minimum of 50% improvement occurs in any of primary voiding diary variables compared with the baseline. For urge incontinence patients, these voiding diary variables may include: number of leaking episodes per day, number of heavy leaking episodes per day, and number of pads used per day. For patients with urgency-frequency, primary voiding diary variables may include: number of voids per day, volume voided per void and degree of urgency experienced before each void. For patients with retention, primary voiding diary variables may include: catheterized volume per catheterization and number of catheterizations per day.

The mechanism of action of SNM is multifactorial and impacts the neuro-axis at several different levels. In patients with OAB, it is believed that pudendal afferents can activate the inhibitory reflexes that promote bladder storage by inhibiting the afferent limb of an abnormal voiding reflex. This blocks input to the pontine micturition center, thereby restricting involuntary detrusor contractions without interfering with normal voiding patterns. For patients with urinary retention, SNM is believed to activate the pudendal nerve afferents originating from the pelvic organs into the spinal cord. At the level of the spinal cord, pudendal afferents may turn on voiding reflexes by suppressing exaggerated guarding reflexes, thus relieving symptoms of patients with urinary retention so normal voiding can be facilitated. In patients with fecal incontinence, it is hypothesized that SNM stimulates pudendal afferent somatic fibers that inhibit colonic propulsive activity and activates the internal anal sphincter, which in turn improves the symptoms of fecal incontinence patients. The present invention relates to a system adapted to deliver neurostimulation to targeted nerve tissues in a manner that disrupts, inhibits, or prevents neural activity in the targeted nerve tissues so as to provide therapeutic effect in treatment of OAB or bladder related dysfunction. In one aspect, the system is adapted to provide therapeutic effect by neurostimulation without inducing motor control of the muscles associated with OAB or bladder related dysfunction by the delivered neurostimulation. In another aspect, the system is adapted to provide such therapeutic effect by delivery of sub-threshold neurostimulation below a threshold that induces paresthesia and/or neuromuscular response or to allow adjustment of neurostimulation to delivery therapy at sub-threshold levels.

B. Positioning Neurostimulation Leads with EMG

While conventional approaches have shown efficacy in treatment of bladder related dysfunction, there exists a need to improve positioning of the neurostimulation leads and consistency between the trial and permanent implantation positions of the lead. Neurostimulation relies on consistently delivering therapeutic stimulation from a pulse generator, via one or more neurostimulation electrodes, to particular nerves or targeted regions. The neurostimulation electrodes are provided on a distal end of an implantable lead that can be advanced through a tunnel formed in patient tissue. Implantable neurostimulation systems provide patients with great freedom and mobility, but it may be easier to adjust the neurostimulation electrodes of such systems before they are surgically implanted. It is desirable for the physician to confirm that the patient has desired motor and/or sensory responses before implanting an IPG. For at least some treatments (including treatments of at least some forms of urinary and/or fecal dysfunction), demonstrating appropriate motor responses may be highly beneficial for accurate and objective lead placement while the sensory response may not be required or not available (e.g., patient is under general anesthesia).

Placement and calibration of the neurostimulation electrodes and implantable leads sufficiently close to specific nerves can be beneficial for the efficacy of treatment. Accordingly, aspects and embodiments of the present disclosure are directed to aiding and refining the accuracy and precision of neurostimulation electrode placement. Further, aspects and embodiments of the present disclosure are directed to aiding and refining protocols for setting therapeutic treatment signal parameters for a stimulation program implemented through implanted neurostimulation electrodes.

Prior to implantation of the permanent device, patients may undergo an initial testing phase to estimate potential response to treatment. As discussed above, PNE may be done under local anesthesia, using a test needle to identify the appropriate sacral nerve(s) according to a subjective sensory response by the patient. Other testing procedures can involve a two-stage surgical procedure, where a quadripolar tined lead is implanted for a testing phase to determine if patients show a sufficient reduction in symptom frequency, and if appropriate, proceeding to the permanent surgical implantation of a neuromodulation device. For testing phases and permanent implantation, determining the location of lead placement can be dependent on subjective qualitative analysis by either or both of a patient or a physician.

In exemplary embodiments, determination of whether or not an implantable lead and neurostimulation electrode is located in a desired or correct location can be accomplished through use of electromyography ("EMG"), also known as surface electromyography. EMG is a technique that uses an EMG system or module to evaluate and record electrical activity produced by muscles, producing a record called an electromyogram. EMG detects the electrical potential generated by muscle cells when those cells are electrically or neurologically activated. The signals can be analyzed to detect activation level or recruitment order. EMG can be performed through the skin surface of a patient, intramuscularly or through electrodes disposed within a patient near target muscles, or using a combination of external and internal structures. When a muscle or nerve is stimulated by an electrode, EMG can be used to determine if the related muscle is activated, (i.e. whether the muscle fully contracts, partially contracts, or does not contract), in response to the stimulus. Accordingly, the degree of activation of a muscle can indicate whether an implantable lead or neurostimulation electrode is located in the desired or correct location on a patient. Further, the degree of activation of a muscle can indicate whether a neurostimulation electrode is providing a stimulus of sufficient strength, amplitude, frequency, or duration to affect a treatment regimen on a patient. Thus, use of EMG provides an objective and quantitative means by which to standardize placement of implantable leads and neurostimulation electrodes, reducing the subjective assessment of patient sensory responses.

In some approaches, positional titration procedures may optionally be based in part on a paresthesia or pain-based subjective response from a patient. In contrast, EMG triggers a measureable and discrete muscular reaction. As the efficacy of treatment often relies on precise placement of the neurostimulation electrodes at target tissue locations and the consistent, repeatable delivery of neurostimulation therapy, using an objective EMG measurement can substantially improve the utility and success of SNM treatment. The measureable muscular reaction can be a partial or a complete muscular contraction, including a response below the triggering of an observable motor response, such as those shown in Table 1, depending on the stimulation of the target muscle. In addition, by utilizing a trial system that allows the neurostimulation lead to remain implanted for use in the permanently implanted system, the efficacy and outcome of the permanently implanted system is more consistent with the results of the trial period, which moreover leads to improved patient outcomes.

C. Example Embodiments

FIG. 1 schematically illustrates an exemplary nerve stimulation system, which includes both a trial neurostimulation system 200 and a permanently implanted neurostimulation system 100, in accordance with aspects of the invention. The EPG 80 and IPG 10 are each compatible with and wirelessly communicate with a clinician programmer 60 and a patient remote 70, which are used in positioning and/or programming the trial neurostimulation system 200 and/or permanently implanted system 100 after a successful trial. As discussed above, the clinician programmer can include specialized software, specialized hardware, and/or both, to aid in lead placement, programming, re-programming, stimulation control, and/or parameter setting. In addition, each of the IPG and the EPG allows the patient at least some control over stimulation (e.g., initiating a pre-set program, increasing or decreasing stimulation), and/or to monitor battery status with the patient remote. This approach also allows for an almost seamless transition between the trial system and the permanent system.

In one aspect, the clinician programmer 60 is used by a physician to adjust the settings of the EPG and/or IPG while the lead is implanted within the patient. The clinician programmer can be a tablet computer used by the clinician to program the IPG, or to control the EPG during the trial period. The clinician programmer can also include capability to record stimulation-induced electromyograms to facilitate lead placement and programming. The patient remote 70 can allow the patient to turn the stimulation on or off, or to vary stimulation from the IPG while implanted, or from the EPG during the trial phase.

In another aspect, the clinician programmer 60 has a control unit which can include a microprocessor and specialized computer-code instructions for implementing methods and systems for use by a physician in deploying the treatment system and setting up treatment parameters. The clinician programmer generally includes a user interface which can be a graphical user interface, an EMG module, electrical contacts such as an EMG input that can couple to an EMG output stimulation cable, an EMG stimulation signal generator, and a stimulation power source. The stimulation cable can further be configured to couple to any or all of an access device (e.g., a foramen needle), a treatment lead of the system, or the like. The EMG input may be configured to be coupled with one or more sensory patch electrode(s) for attachment to the skin of the patient adjacent a muscle (e.g., a muscle enervated by a target nerve). Other connectors of the clinician programmer may be configured for coupling with an electrical ground or ground patch, an electrical pulse generator (e.g., an EPG or an IPG), or the like. As noted above, the clinician programmer can include a module with hardware and computer-code to execute EMG analysis, where the module can be a component of the control unit microprocessor, a pre-processing unit coupled to or in-line with the stimulation and/or sensory cables, or the like.

In some aspects, the clinician programmer is configured to operate in combination with an EPG when placing leads in a patient body. The clinician programmer can be electronically coupled to the EPG during test simulation through a specialized cable set. The test simulation cable set can connect the clinician programmer device to the EPG and allow the clinician programmer to configure, modify, or otherwise program the electrodes on the leads connected to the EPG.

The electrical pulses generated by the EPG and IPG are delivered to one or more targeted nerves via one or more neurostimulation electrodes at or near a distal end of each of one or more leads. The leads can have a variety of shapes, can be a variety of sizes, and can be made from a variety of materials, which size, shape, and materials can be tailored to the specific treatment application. While in this embodiment, the lead is of a suitable size and length to extend from the IPG and through one of the foramen of the sacrum to a targeted sacral nerve, in various other applications, the leads may be, for example, implanted in a peripheral portion of the patient's body, such as in the arms or legs, and can be configured to deliver electrical pulses to the peripheral nerve such as may be used to relieve chronic pain. It is appreciated that the leads and/or the stimulation programs may vary according to the nerves being targeted.

Figure 2A:
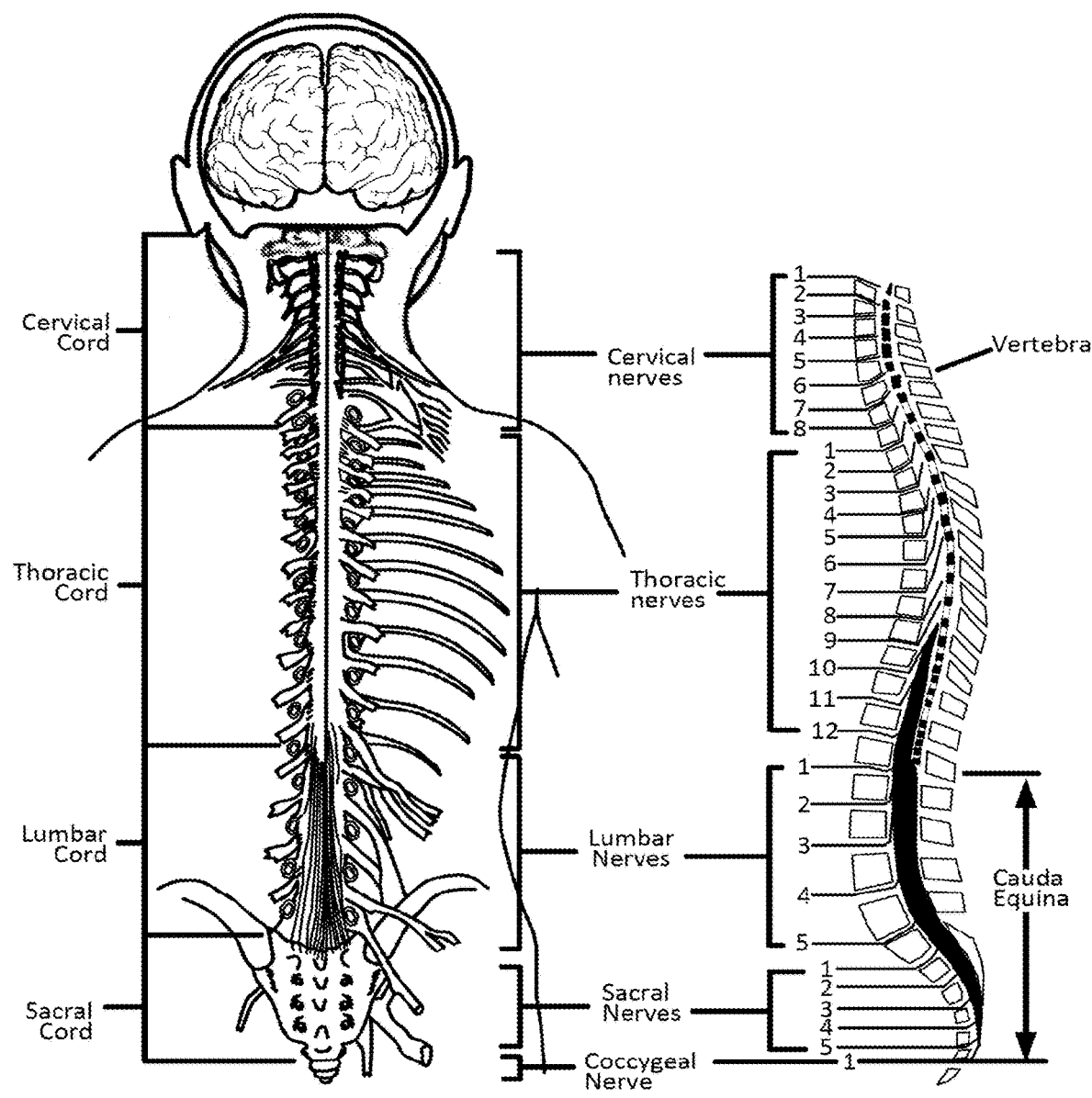
FIGS. 2A-2C show diagrams of the nerve structures along the spine, the lower back and sacrum region, which may be stimulated in accordance with aspects of the invention.
Figure 2B:
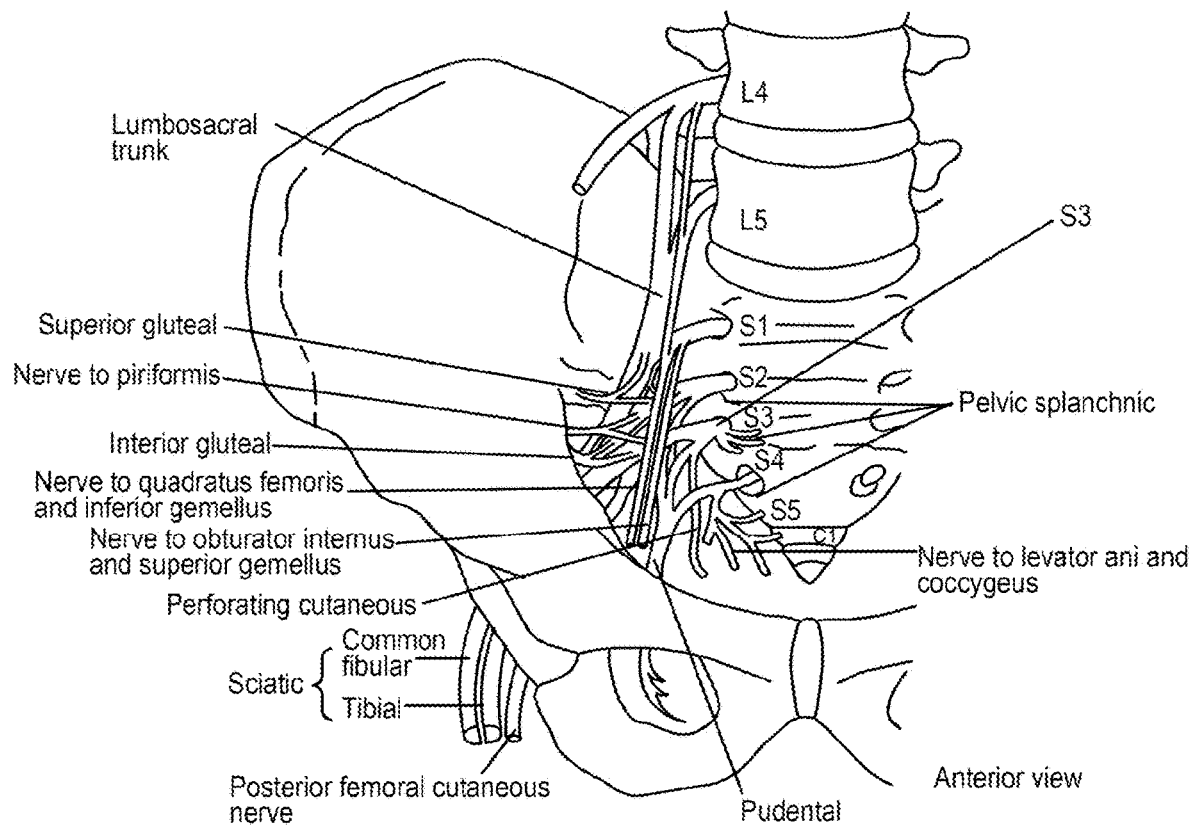
Figure 2C:
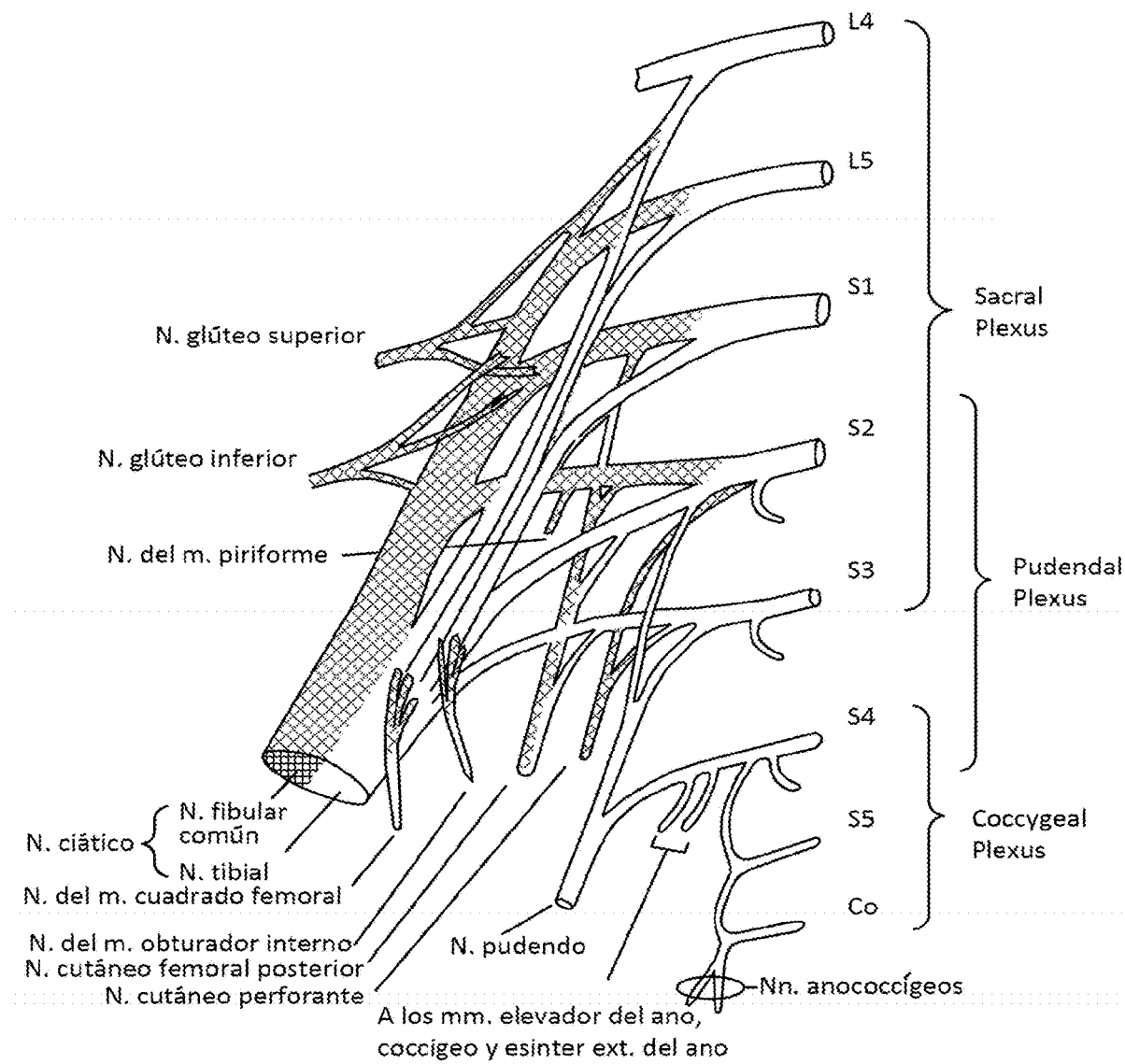

FIGS. 2A-2C show diagrams of various nerve structures of a patient, which may be used in neurostimulation treatments, in accordance with aspects of the invention. FIG. 2A shows the different sections of the spinal cord and the corresponding nerves within each section. The spinal cord is a long, thin bundle of nerves and support cells that extend from the brainstem along the cervical cord, through the thoracic cord and to the space between the first and second lumbar vertebra in the lumbar cord. Upon exiting the spinal cord, the nerve fibers split into multiple branches that innervate various muscles and organs transmitting impulses of sensation and control between the brain and the organs and muscles. Since certain nerves may include branches that innervate certain organs, such as the bladder, and branches that innervate certain muscles of the leg and foot, stimulation of the nerve at or near the nerve root near the spinal cord can stimulate the nerve branch that innervate the targeted organ, which may also result in muscle responses associated with the stimulation of the other nerve branch. Thus, by monitoring for certain muscle responses, such as those in Table 1, either visually, through the use of EMG as described herein or both, the physician can determine whether the targeted nerve is being stimulated. While stimulation at a certain threshold may trigger the noted muscle responses, stimulation at a sub-threshold level may still provide stimulation to the nerve associated with the targeted organ without causing the corresponding muscle response, and in some embodiments, without causing any paresthesia. This is advantageous as it allows for treatment of the condition by neurostimulation without otherwise causing patient discomfort, pain or undesired muscle responses.

FIG. 2B shows the nerves associated with the lower back section, in the lower lumbar cord region where the nerve bundles exit the spinal cord and travel through the sacral foramens of the sacrum. In some embodiments, the neurostimulation lead is advanced through the foramen until the neurostimulation electrodes are positioned at the anterior sacral nerve root, while the anchoring portion of the lead proximal of the stimulation electrodes are generally disposed dorsal of the sacral foramen through which the lead passes, so as to anchor the lead in position. FIG. 2C shows detail views of the nerves of the lumbosacral trunk and the sacral plexus, in particular, the S1-S5 nerves of the lower sacrum. The S3 sacral nerve is of particular interest for treatment of bladder-related dysfunction, and in particular OAB.

FIG. 3A schematically illustrates an example of a fully implanted neurostimulation system 100 adapted for sacral nerve stimulation. Neurostimulation system 100 includes an IPG implanted in a lower back region and connected to a neurostimulation lead extending through the S3 foramen for stimulation of the S3 sacral nerve. The lead is anchored by a tined anchor portion 30 that maintains a position of a set of neurostimulation electrodes 40 along the targeted nerve, which in this example, is the anterior sacral nerve root S3 which enervates the bladder so as to provide therapy for various bladder related dysfunctions. While this embodiment is adapted for sacral nerve stimulation, it is appreciated that similar systems can be used in treating patients with, for example, chronic, severe, refractory neuropathic pain originating from peripheral nerves or various urinary dysfunctions or still further other indications. Implantable neurostimulation systems can be used to either stimulate a target peripheral nerve or the posterior epidural space of the spine.

Properties of the electrical pulses can be controlled via a controller of the implanted pulse generator. In some embodiments, these properties can include, for example, the frequency, strength, pattern, duration, or other aspects of the electrical pulses. These properties can include, for example, a voltage, a current, or the like. This control of the electrical pulses can include the creation of one or more electrical pulse programs, plans, or patterns, and in some embodiments, this can include the selection of one or more preexisting electrical pulse programs, plans, or patterns. In the embodiment depicted in FIG. 3A, the implantable neurostimulation system 100 includes a controller in the IPG having one or more pulse programs, plans, or patterns that may be pre-programmed or created as discussed above. In some embodiments, these same properties associated with the IPG may be used in an EPG of a partly implanted trial system used before implantation of the permanent neurostimulation system 100.

Figure 3B:
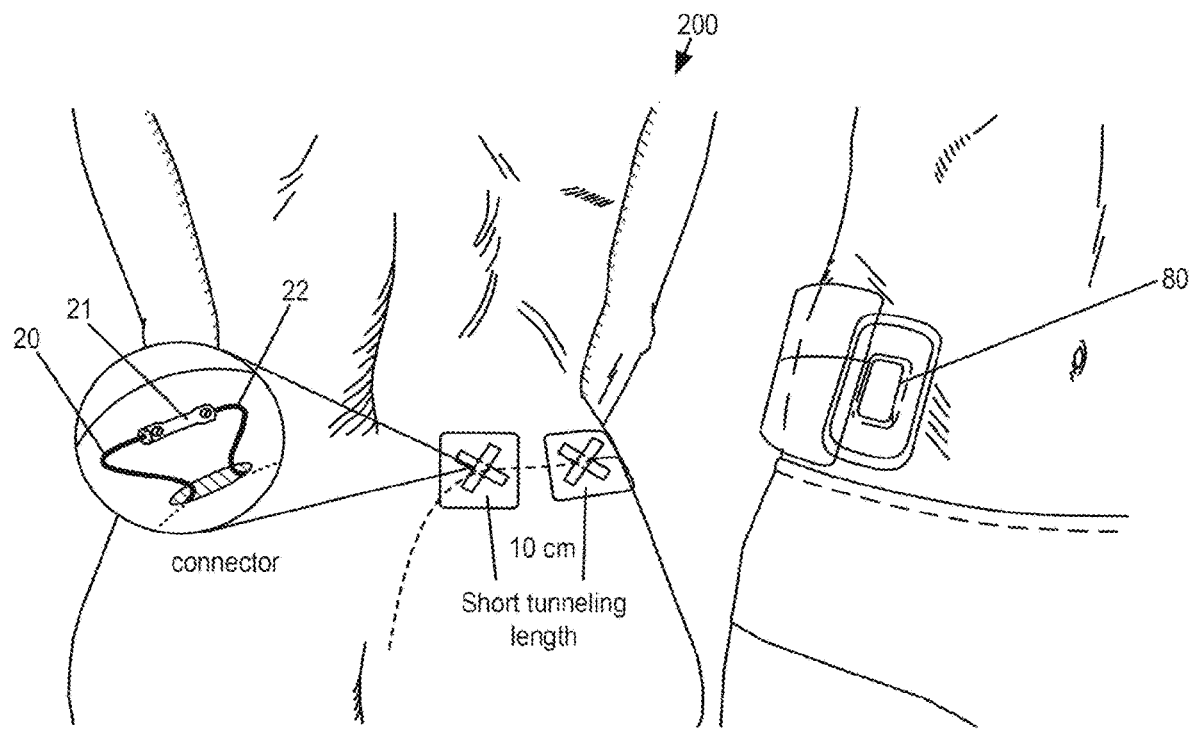
FIG. 3B shows an example of a neurostimulation system having a partly implanted stimulation lead and an external pulse generator adhered to the skin of the patient for use in a trial stimulation, in accordance with aspects of the invention.
Figure 3B:
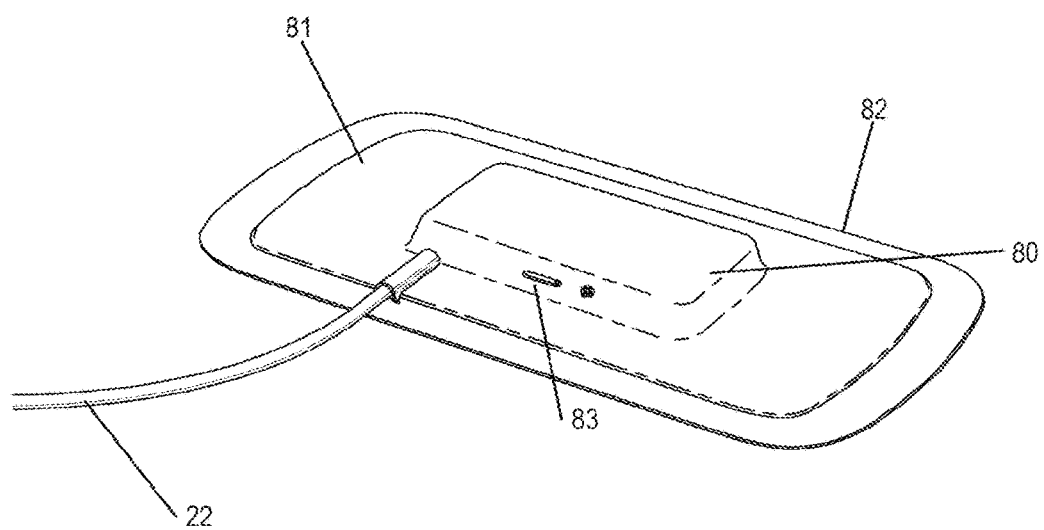

FIG. 3B shows a schematic illustration of a trial neurostimulation system 200 utilizing an EPG patch 81 adhered to the skin of a patient, particularly to the abdomen of a patient, the EPG 80 being encased within the patch. In one aspect, the lead is hardwired to the EPG, while in another the lead is removably coupled to the EPG through a port or aperture in the top surface of the flexible patch 81. Excess lead can be secured by an additional adherent patch. In one aspect, the EPG patch is disposable such that the lead can be disconnected and used in a permanently implanted system without removing the distal end of the lead from the target location. Alternatively, the entire system can be disposable and replaced with a permanent lead and IPG. When the lead of the trial system is implanted, an EMG obtained via the clinician programmer using one or more sensor patches can be used to ensure that the leads are placed at a location proximate to the target nerve or muscle, as discussed previously.

In some embodiments, the trial neurostimulation system utilizes an EPG 80 within an EPG patch 81 that is adhered to the skin of a patient and is coupled to the implanted neurostimulation lead 20 through a lead extension 22, which is coupled with the lead 20 through a connector 21. This extension and connector structure allows the lead to be extended so that the EPG patch can be placed on the abdomen and allows use of a lead having a length suitable for permanent implantation should the trial prove successful. This approach may utilize two percutaneous incisions, the connector provided in the first incision and the lead extensions extending through the second percutaneous incision, there being a short tunneling distance (e.g., about 10 cm) therebetween. This technique may also minimize movement of an implanted lead during conversion of the trial system to a permanently implanted system.

In one aspect, the EPG unit is wirelessly controlled by a patient remote and/or the clinician programmer in a similar or identical manner as the IPG of a permanently implanted system. The physician or patient may alter treatment provided by the EPG through use of such portable remotes or programmers and the treatments delivered are recorded on a memory of the programmer for use in determining a treatment suitable for use in a permanently implanted system. The clinician programmer can be used in lead placement, programming and/or stimulation control in each of the trial and permanent nerve stimulation systems. In addition, each nerve stimulation system allows the patient to control stimulation or monitor battery status with the patient remote. This configuration is advantageous as it allows for an almost seamless transition between the trial system and the permanent system. From the patient's viewpoint, the systems will operate in the same manner and be controlled in the same manner, such that the patient's subjective experience in using the trial system more closely matches what would be experienced in using the permanently implanted system. Thus, this configuration reduces any uncertainties the patient may have as to how the system will operate and be controlled such that the patient will be more likely to convert a trial system to a permanent system.

As shown in the detailed view of FIG. 3B, the EPG 80 is encased within a flexible laminated patch 81, which includes an aperture or port through which the EPG 80 is connected to the lead extension 22. The patch may further include an "on/off" button 83 with a molded tactile detail to allow the patient to turn the EPG on and/or off through the outside surface of the adherent patch 81. The underside of the patch 81 is covered with a skin-compatible adhesive 82 for continuous adhesion to a patient for the duration of the trial period. For example, a breathable strip having skin-compatible adhesive 82 would allow the EPG 80 to remain attached to the patient continuously during the trial, which may last over a week, typically two weeks to four weeks, or even longer.

Figure 4:
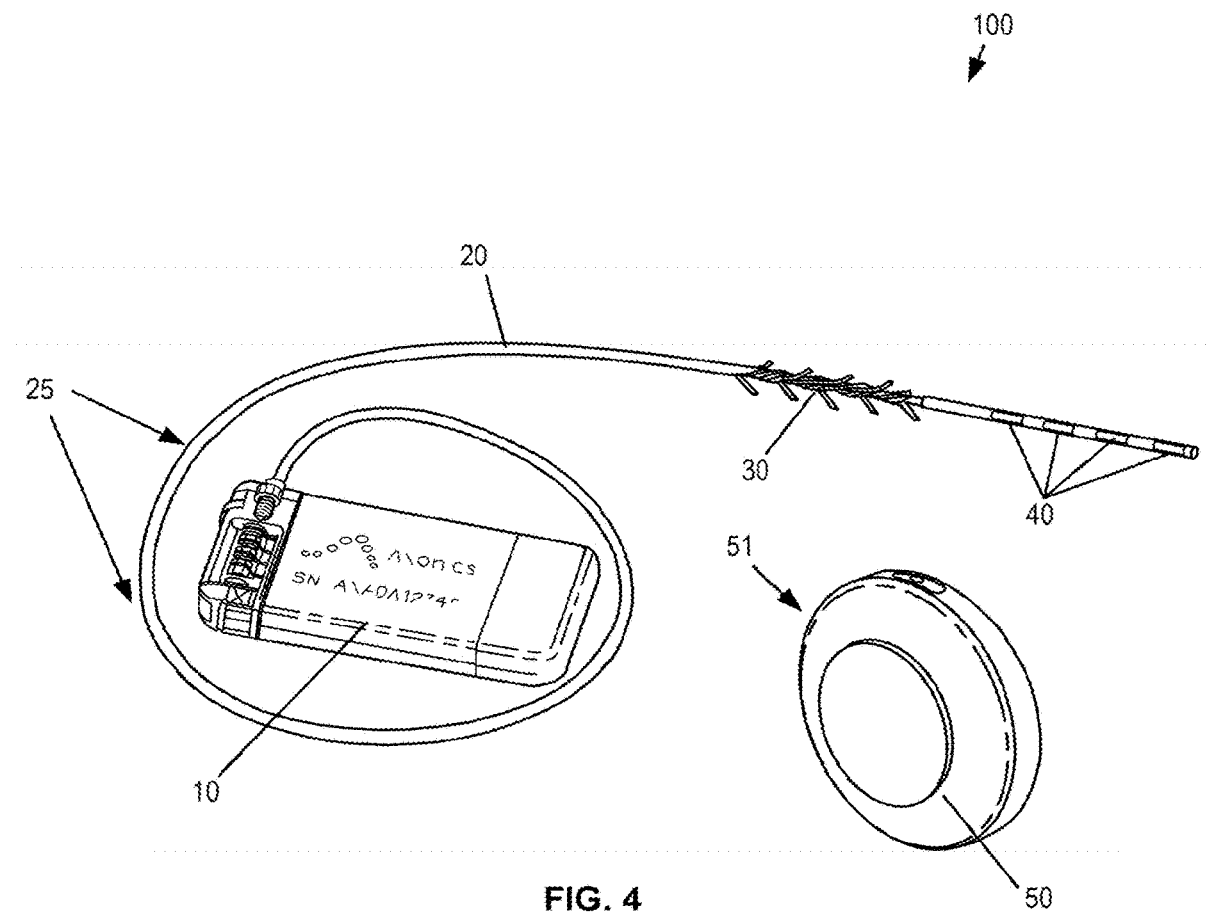
FIG. 4 shows an example of a neurostimulation system having an implantable stimulation lead, an implantable pulse generator, and an external charging device, in accordance with aspects of the invention.

FIG. 4 illustrates an example neurostimulation system 100 that is fully implantable and adapted for sacral nerve stimulation treatment. The implantable system 100 includes an IPG 10 that is coupled to a neurostimulation lead 20 that includes a group of neurostimulation electrodes 40 at a distal end of the lead. As seen in FIG. 4, the lead is coupled to the header portion 11, the titanium case portion 17, and/or the ceramic case portion 14 of the housing of the IPG 10 via the connector stack and/or the strain relief. The lead includes a lead anchor portion 30 with a series of tines extending radially outward so as to anchor the lead and maintain a position of the neurostimulation lead 20 after implantation. The lead 20 may further include one or more radiopaque markers 25 to assist in locating and positioning the lead using visualization techniques such as fluoroscopy. In some embodiments, the IPG provides monopolar or bipolar electrical pulses that are delivered to the targeted nerves through one or more neurostimulation electrodes, typically four electrodes. In sacral nerve stimulation, the lead is typically implanted through the S3 foramen as described herein.

The IPG can be rechargeable or non-rechargeable. In one aspect, the IPG is rechargeable wirelessly through conductive coupling by use of a charging device 50 (CD), which is a portable device powered by a rechargeable battery to allow patient mobility while charging. The CD 50 is used for transcutaneous charging of the IPG through RF induction. The CD 50 can either be either patched to the patient's skin using an adhesive or can be held in place using a belt 53 or by an adhesive patch 52. The CD 50 may be charged by plugging the CD directly into an outlet or by placing the CD in a charging dock or station 51 that connects to an AC wall outlet or other power source.

The CD 50 can include a housing 51. The housing 51 can comprise a variety of shapes and sizes. In some embodiments, the housing 51 can be cylindrically shaped as shown in FIG. 4, and specifically, can comprise a plurality of connected cylindrical portions, wherein the connected cylindrical portions have different diameters and/or lengths. In some embodiments, the housing 51 can be a metal or polymer such as a plastic or the like.

The CD 50 can include a processor and/or memory adapted to provide instructions to and receive information from the other components of the implantable neurostimulation system. The processor can include a microprocessor, such as a commercially available microprocessor from Intel® or Advanced Micro Devices, Inc.®, or the like. The CD 50 may include an energy storage feature, such as one or more capacitors, and typically includes a wireless charging unit. Some details of CD 50 will be discussed at greater lengths below with respect to FIG. 7.

The system may further include a patient remote 70 and clinician programmer 60, each configured to wirelessly communicate with the implanted IPG, or with the EPG during a trial. The clinician programmer 60 may be a tablet computer used by the clinician to program the IPG and the EPG. The device also has the capability to record stimulation-induced electromyograms (EMGs) to facilitate lead placement, programming, and/or re-programming. The patient remote may be a battery-operated, portable device that utilizes radio-frequency (RF) signals to communicate with the EPG and IPG and allows the patient to adjust the stimulation levels, check the status of the IPG battery level, and/or to turn the stimulation on or off.

Figure 5A:
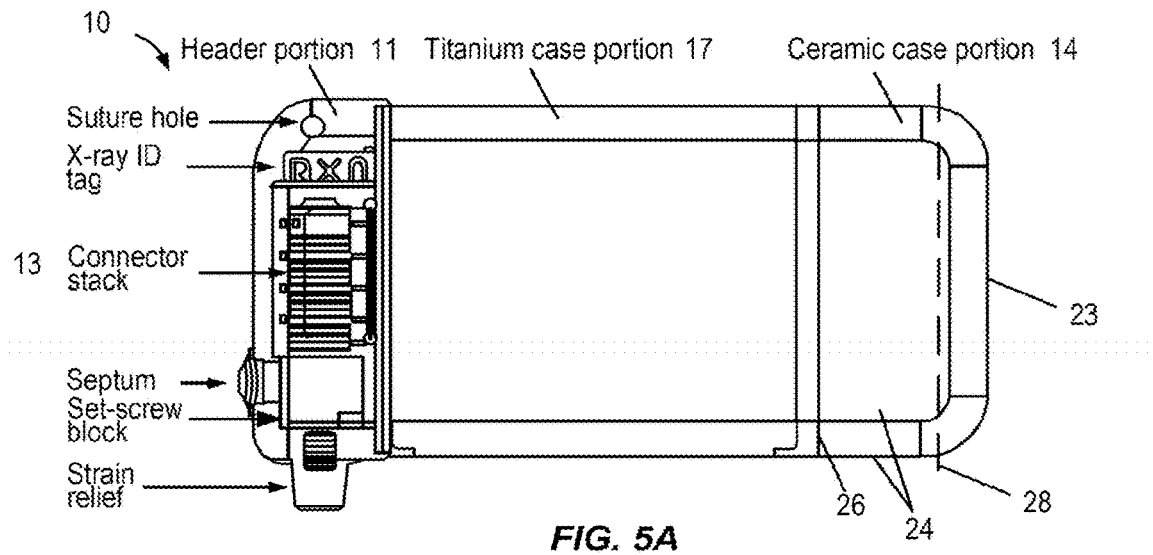
FIGS. 5A-5C show detail views of an implantable pulse generator and associated components for use in a neurostimulation system, in accordance with aspects of the invention.
Figure 5B:
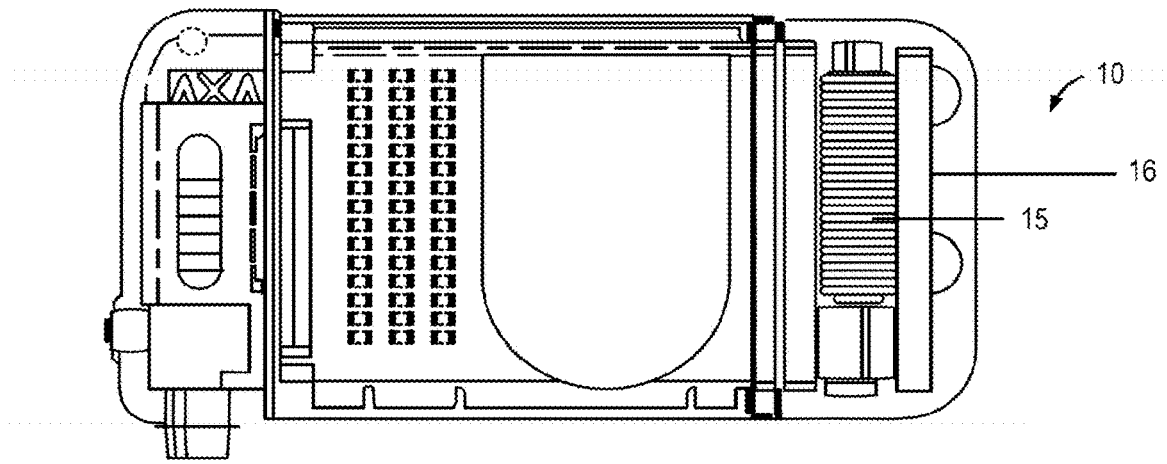
Figure 5C:
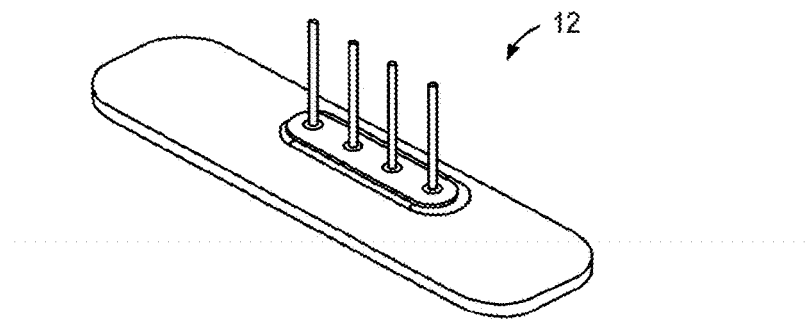

FIG. 5A-5C show detail views of the IPG and its internal components. In some embodiments, the pulse generator can generate one or more non-ablative electrical pulses that are delivered to a nerve to control pain or cause some other desired effect, for example to inhibit, prevent, or disrupt neural activity for the treatment of OAB or bladder related dysfunction. In some applications, the pulses having a pulse amplitude in a range between 0 mA to 1,000 mA, 0 mA to 100 mA, 0 mA to 50 mA, 0 mA to 25 mA, and/or any other or intermediate range of amplitudes may be used. One or more of the pulse generators can include a processor and/or memory adapted to provide instructions to and receive information from the other components of the implantable neurostimulation system. The processor can include a microprocessor, such as a commercially available microprocessor from Intel® or Advanced Micro Devices, Inc.®, or the like. An IPG may include an energy storage feature, such as one or more capacitors, and typically includes a wireless charging unit.

One or more properties of the electrical pulses can be controlled via a controller of the IPG or EPG. In some embodiments, these properties can include, for example, the frequency, strength, pattern, duration, or other aspects of the timing and magnitude of the electrical pulses. These properties can further include, for example, a voltage, a current, or the like. This control of the electrical pulses can include the creation of one or more electrical pulse programs, plans, or patterns, and in some embodiments, this can include the selection of one or more pre-existing electrical pulse programs, plans, or patterns. In one aspect, the IPG 100 includes a controller having one or more pulse programs, plans, or patterns that may be created and/or pre-programmed. In some embodiments, the IPG can be programmed to vary stimulation parameters including pulse amplitude in a range from 0 mA to 10 mA, pulse width in a range from 50 μs to 500 μs, pulse frequency in a range from 5 Hz to 250 Hz, stimulation modes (e.g., continuous or cycling), and electrode configuration (e.g., anode, cathode, or off), to achieve the optimal therapeutic outcome specific to the patient. In particular, this allows for an optimal setting to be determined for each patient even though each parameter may vary from person to person.

As shown in FIGS. 5A-5B, the IPG may include a header portion 11 at one end and a ceramic portion 14 at the opposite end. The header portion 11 houses a feed-through assembly 12 and connector stack 13, while the ceramic case portion 14 houses an antennae assembly 16 to facilitate wireless communication with the clinician program, and/or the patient remote. The ceramic case portion 14 can, in embodiments in which the IPG is rechargeable, house a charging coil to facilitate wireless charging with the CD. The remainder of the IPG is covered with a titanium case portion 17, which encases the printed circuit board, memory and controller components that facilitate the electrical pulse programs described above. The ceramic portion 14 includes an end 23, sides 24, and a connection portion 26 that connects the ceramic portion 14 to the case portion 17. In the example shown in FIG. 5B, the antennae assembly 16 is positioned such that a plane 28, in which loops of a radiating element lay, is perpendicular to and extends through the sides 24 of the ceramic portion 14.

In the example shown in FIG. 5C, the header portion of the IPG includes a four-pin feed-through assembly 12 that couples with the connector stack 13 in which the proximal end of the lead is coupled. The four pins correspond to the four electrodes of the neurostimulation lead. In some embodiments, a Balseal® connector block is electrically connected to four platinum/iridium alloy feed-through pins which are brazed to an alumina ceramic insulator plate along with a titanium alloy flange. This feed-through assembly is laser seam welded to a titanium-ceramic brazed case to form a complete hermetic housing for the electronics. In some embodiments, some or all of the pieces of the IPG 10 forming the hermetic housing can be biocompatible, and specifically, can have external surfaces made of biocompatible materials.

In some embodiments, such as that shown in FIG. 5A, the ceramic and titanium brazed case is utilized on one end of the IPG where the ferrite coil and PCB antenna assemblies are positioned. A reliable hermetic seal is provided via a ceramic-to-metal brazing technique. The zirconia ceramic may comprise a 3Y-TZP (3 mol percent Yttria-stabilized tetragonal Zirconia Polycrystals) ceramic, which has a high flexural strength and impact resistance and has been commercially utilized in a number of implantable medical technologies. It will be appreciated, however, that other ceramics or other suitable materials may be used for construction of the IPG, and that ceramic may be used to form additional portions of the case.

In one aspect, utilization of ceramic material provides an efficient, radio-frequency-transparent window for wireless communication with the external patient remote and clinician's programmer as the communication antenna is housed inside the hermetic ceramic case. This ceramic window has further facilitated miniaturization of the implant while maintaining an efficient, radio-frequency-transparent window for long term and reliable wireless communication between the IPG and external controllers, such as the patient remote and clinician programmer. The IPG's wireless communication is generally stable over the lifetime of the device, unlike prior art products where the communication antenna is placed in the header outside the hermetic case. The communication reliability of such prior art devices tends to degrade due to the change in dielectric constant of the header material in the human body over time.

In some embodiments, the ferrite core is part of the charging coil assembly 15, shown in FIG. 5B, which can be positioned inside the ceramic case 14. The ferrite core concentrates the magnetic field flux through the ceramic case as opposed to the metallic case portion 17. This configuration maximizes coupling efficiency, which reduces the required magnetic field and in turn reduces device heating during charging. In particular, because the magnetic field flux is oriented in a direction perpendicular to the smallest metallic cross section area, heating during charging is minimized. This configuration also allows the IPG to be effectively charged at a depth of 3 cm with the CD, when positioned on a skin surface of the patient near the IPG, and reduces re-charging time.

Figure 6:
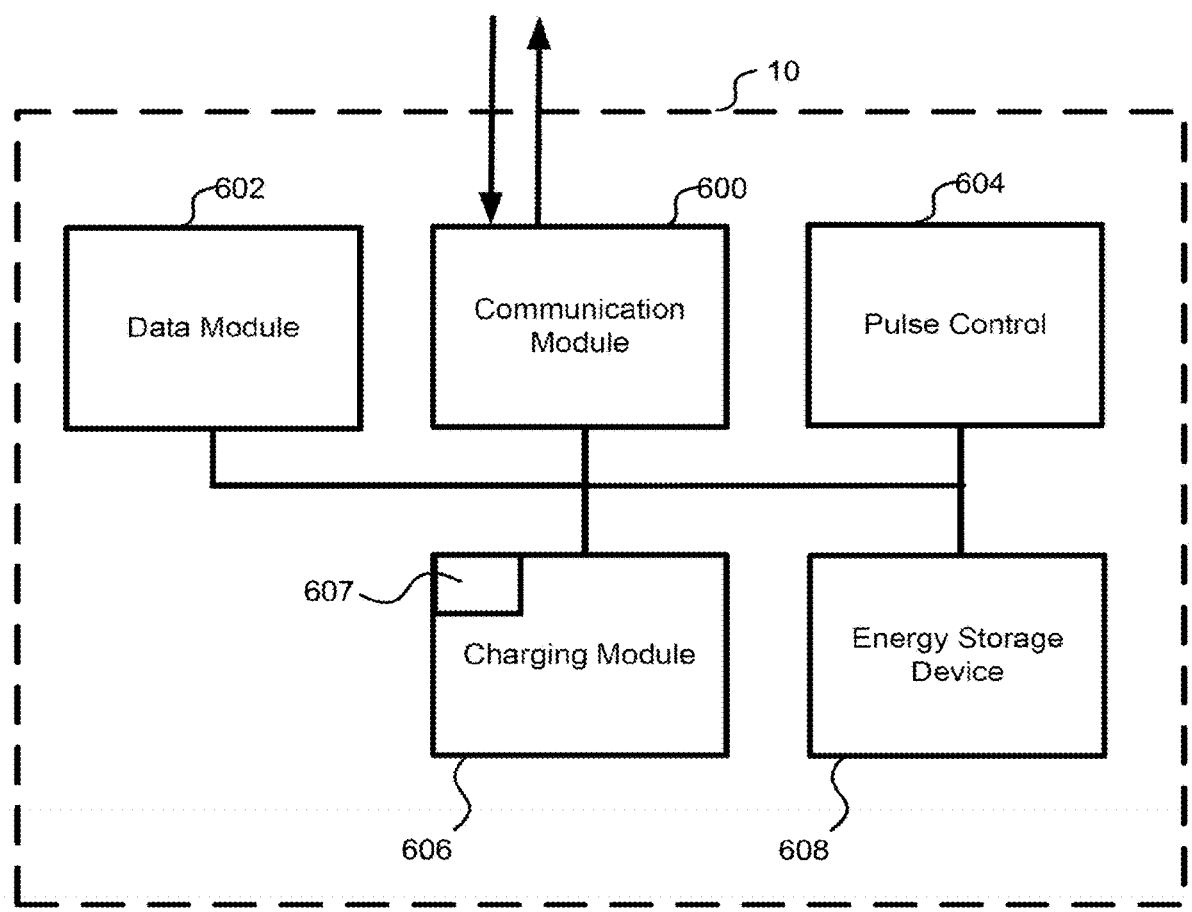
FIG. 6 shows a schematic illustration of one embodiment of the architecture of the IPG.

FIG. 6 shows a schematic illustration of one embodiment of the architecture of the IPG 10. In some embodiments, each of the components of the architecture of the IPG 10 can be implemented using the processor, memory, and/or other hardware component of the IPG 10. In some embodiments, the components of the architecture of the IPG 10 can include software that interacts with the hardware of the IPG 10 to achieve a desired outcome, and the components of the architecture of the IPG 10 can be located within the housing.

In some embodiments, the IPG 10 can include, for example, a communication module 600. The communication module 600 can be configured to send data to and receive data from other components and/or devices of the exemplary nerve stimulation system including, for example, the clinician programmer 60, the charging device 50, and/or the patient remote 70. In some embodiments, the communication module 600 can include one or several antennas and software configured to control the one or several antennas to send information to and receive information from one or several of the other components of the IPG 10. In some embodiments, for example, when connecting with the charging device 50, the communications module 600 can be configured to send data identifying the IPG 10 and/or characterizing one or several attributes of the IPG 10. In some embodiments, this information can be, for example, a number uniquely identifying the IPG 10 such as, for example, a serial number, or the like. In some embodiments, this data can characterize one or several attributes of the IPG 10 such as, for example, the natural frequency of a charging module 606 of the IPG 10 and/or of one or several components of the charging module 606 of the IPG.

The IPG 10 can further include a data module 602. The data module 602 can be configured to manage data relating to the identity and properties of the IPG 10. In some embodiments, the data module can include one or several databases that can, for example, include information relating to the IPG 10 such as, for example, the identification of the IPG 10, one or several properties of the IPG 10, or the like. In one embodiment, the data identifying the IPG 10 can include, for example, a serial number of the IPG 10 and/or other identifier of the IPG 10 including, for example, a unique identifier of the IPG 10. In some embodiments, the information associated with the property of the IPG 10 can include, for example, data identifying the function of the IPG 10, data identifying the power consumption of the IPG 10, data identifying the charge capacity of the IPG 10 and/or power storage capacity of the IPG 10, data identifying potential and/or maximum rates of charging of the IPG 10, and/or the like. In some embodiments, the information associated with the property of the IPG 10 can include, for example, data identifying the natural frequency of the IPG 10 and/or components thereof. In some embodiments, this information identifying the natural frequency can be generated at the time of the manufacture of the IPG 10.

The IPG 10 can include a pulse control 604. In some embodiments, the pulse control 604 can be configured to control the generation of one or several pulses by the IPG 10. In some embodiments, for example, this can be performed based on information that identifies one or several pulse patterns, programs, or the like. This information can further specify, for example, the frequency of pulses generated by the IPG 10, the duration of pulses generated by the IPG 10, the strength and/or magnitude of pulses generated by the IPG 10, or any other details relating to the creation of one or several pulses by the IPG 10. In some embodiments, this information can specify aspects of a pulse pattern and/or pulse program, such as, for example, the duration of the pulse pattern and/or pulse program, and/or the like. In some embodiments, the pulse control 604 can be configured to determine an impedance of the tissue of the patient, and specifically of the target tissue of the patient. In some embodiments, this determination of impedance can be periodically and/or repeatedly performed. In some embodiments, the impedance of the tissue can be measured after a predetermined number of stimulation pulses have been delivered, and in some embodiments, the impedance of the tissue can be determined with the delivery of each stimulation pulse. In some embodiments, the impedance of the tissue can be determined at the beginning of the delivery of a stimulation pulse. In some embodiments, information relating to and/or for controlling the pulse generation of the IPG 10 can be stored within the memory of the IPG 10.

In some embodiments in which the IPG 10 is rechargeable, the IPG 10 can include a charging module 606. In some embodiments, the charging module 606 can be configured to control and/or monitor the charging/recharging of the IPG 10. In some embodiments, for example, the charging module 606 can include one or several features configured to receive energy for recharging the IPG 10 such as, for example, one or several inductive coils/features that can interact with one or several inductive coils/features of the charging device 50 to create an inductive coupling to thereby recharge the IPG 10. In some embodiments, the charging module 606 can include hardware and/or software configured to monitor the charging of the IPG 10 including, for example, the charging coil assembly 15, also referred to herein as the receiving coil assembly 15 or the elongate receiving coil assembly 15.

The charging module 606 of the IPG 10 can include a charging circuit 607, also referred to herein as the resonant circuit 607, the secondary charging circuit 607, the secondary resonant circuit 607, the receiving charging circuit 607, or the receiving resonant circuit 607. In some embodiments, the charging circuit 607 can comprise, for example, at least one of: an inductor; a capacitor; or a resistor. The charging circuit 607 can be characterized by a natural frequency, which natural frequency can be determined at, for example, the time of assembly of the charging circuit 607 or after the implantation of the IPG 10 in the body. In some embodiments, because of the relatively constant temperature and environment in the body, the natural frequency of the charging circuit 607 can remain constant after the implantation of the IPG 10 into the body.

The IPG 10 can include an energy storage device 608. The energy storage device 608, which can include the energy storage features, can be any device configured to store energy and can include, for example, one or several batteries, capacitors, fuel cells, or the like. In some embodiments, the energy storage device 608 can be configured to receive charging energy from the charging module 606.

Figure 7:
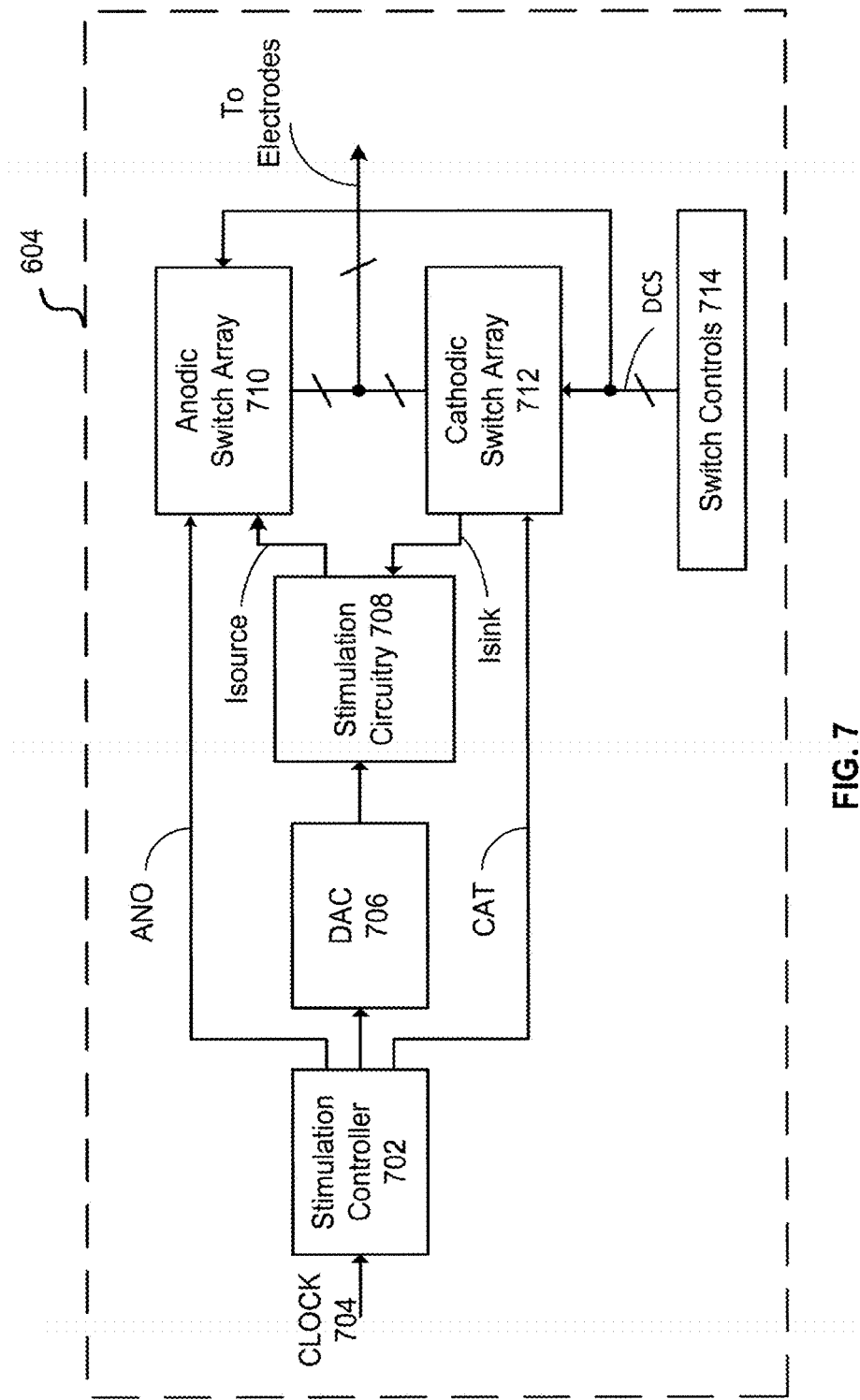
FIG. 7 shows a schematic illustration of one embodiment of the pulse control module.

FIG. 7 shows a schematic illustration of one embodiment of components of the pulse control module 604. The pulse control module 604 includes a stimulation controller 702, a digital to analog converter DAC 706, stimulation circuitry 708, an anodic switch array 710, a cathodic switch array 712, and switch controls 714. Although a single box depicting the stimulation circuitry 708 is shown, the stimulation circuitry 708 can comprises multiple circuits and/or components configured to selectively connect the stimulation circuitry 708 to at least one of the leads to thereby allow the sourcing/sinking of current to or from the at least one of the leads. In some embodiments, the stimulation circuitry 708 can comprise a plurality of circuits including, for example, a first circuit and a second circuit, and in some embodiments, each of the anodic switch array 710 and the cathodic switch array 712 can comprise a plurality of switches.

The pulse control module 604 provides for the sourcing and sinking of current to one or several leads, and/or one or several electrodes on the leads. In some embodiments, this can include sourcing current to at least one lead and/or at least one electrode on at least one lead, and completing a circuit through the target tissue by sinking current from at least one lead and/or at least one electrode on at least one lead. In some embodiments, multiple currents can be sourced to one or several leads and/or electrodes, and similarly, in some embodiments, multiple currents can be sinked from one or several leads and/or electrodes. In some embodiments, the amount of sinked current can match the amount of sourced current.

The pulse control module 604 can, in some embodiments, include both an anodic switch array 710 and a cathodic switch array 712. The pulse control module 604 provides for selecting one or several electrodes for stimulation based upon tissue stimulation requirements determined by a clinician. This selection is made by a combination of the switch arrays 710, 712 and the switch controls 714. The outputs of the switch arrays 710, 712 are selected by setting the corresponding "bits" in switch controls 714. Switch controls 714 generate digital control signals DCS, which control the switching of switch arrays 710, 712 to select one or several electrodes for delivery of stimulation.

In some embodiments, the switch controls 714 can store information regarding stimulation pulse duration, amplitude and profile as well as other operational parameters. Based upon information stored in switch controls 714 and the CLOCK signal 704, stimulation controller 702 generates the desired stimulation pulse amplitude and triggers digital to analog converter DAC 706 to generate an output. Based upon the DAC 706 output, the stimulation circuitry 708 provides a sink for $I_{sink}$ current and provides a source current $I_{source}$.

Figure 8:
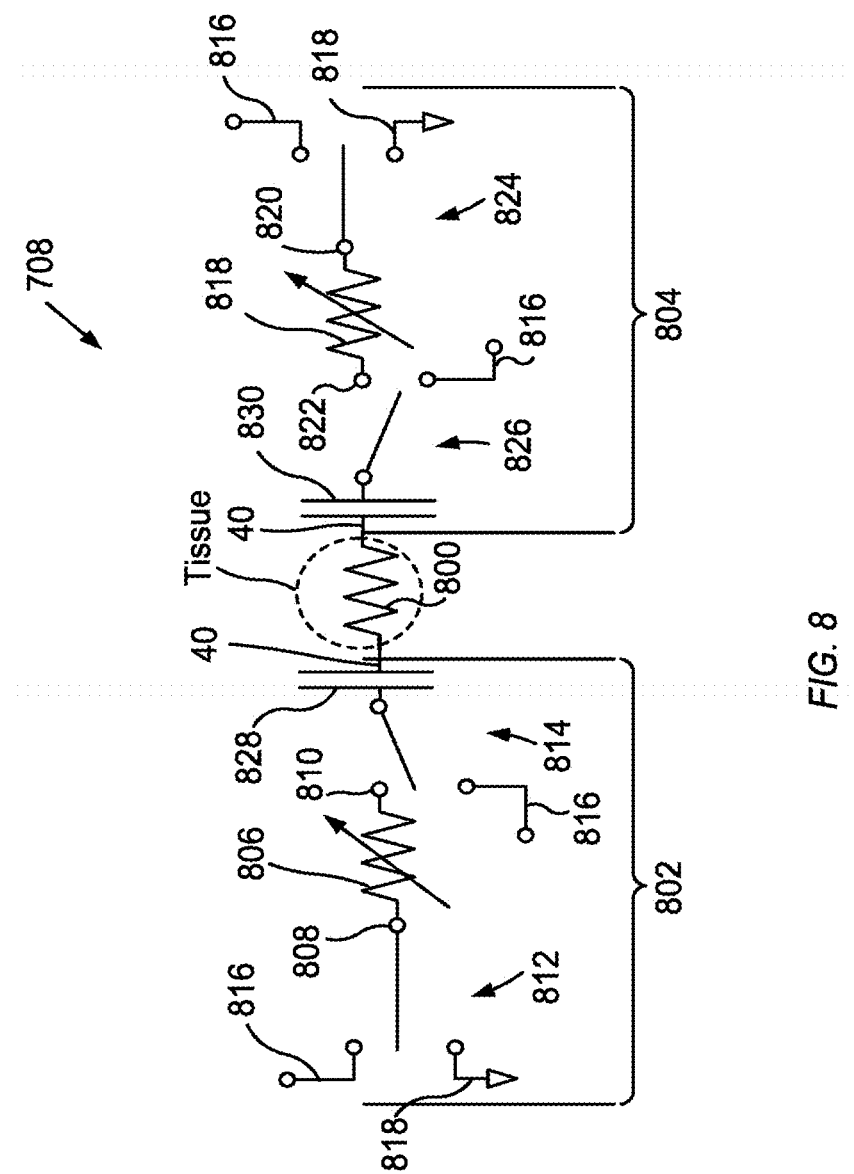
FIG. 8 is a schematic depiction of one embodiment of stimulation circuitry of an implantable pulse generator.

FIG. 8 depicts a schematic illustration of one embodiment of the stimulation circuitry 708 creating a circuit target tissue of a patient, the tissue represented by resistor 800. The stimulation circuitry 708 includes circuits, and specifically includes a first circuit 802 and a second circuit 804. As shown in FIG. 8, all or portions of one or more of the circuits of the stimulation circuitry 708 are connected to the tissue 800 via electrodes 40 that are part of lead 20. In some embodiments, one or more of the electrodes 40 can be coupled, and more specifically can be selectively and/or switchably coupled, to one or more of the circuits 802, 802 via the switch array 710, 712.

Figure 9:
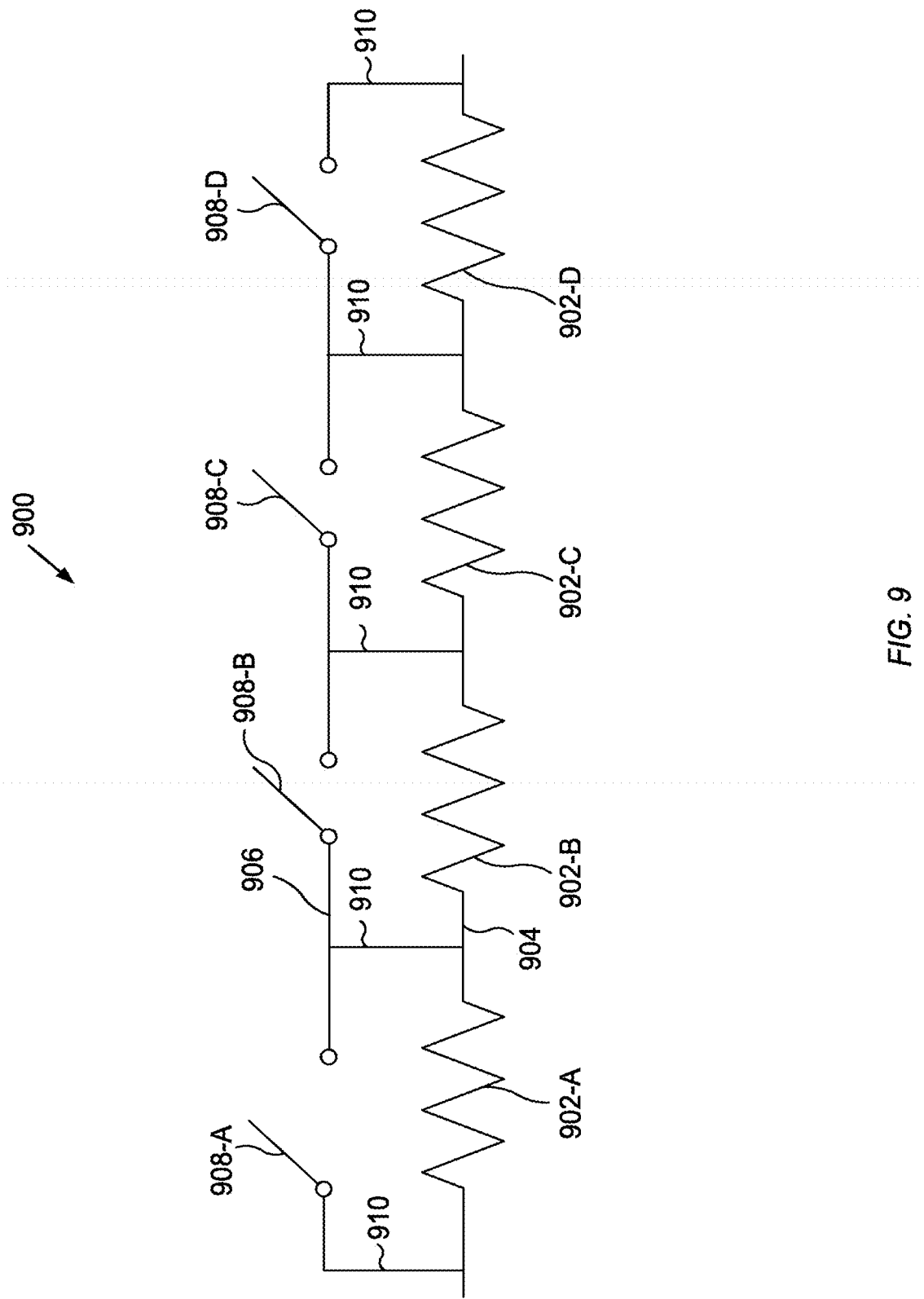
FIG. 9 is a schematic depiction of one embodiment of a bank of switchably connectable resistors.

The first circuit 802 can include an adjustable resistance element 806 having a first terminal 808 and a second terminal 810. The adjustable resistance element 806 can be controlled to have a desired resistance, and can be, in some embodiments, a variable resistor that can be a potentiometer, and/or a rheostat. In some embodiments, the adjustable resistance element 806 can be a digital resistor, and/or a bank of switchably connectable resistors. In some embodiments, the digital resistor and/or the bank of switchably connectable resistors can create a digital first circuit 802 in that resistance of the adjustable resistance element can set at one or several discrete resistance levels. One embodiment of a bank of switchably connectable resistors 900 is shown in FIG. 9. The bank of resistors 900 can further comprise a first path 904 and a second path 906 that is parallel to the first path 904. The first path 904 of the bank of resistors 900 can include a plurality of resistors 902-A, 902-B, 902-C, 902-D. In some embodiments, each of resistors 902 can have the same resistance, and in some embodiments, some or all of resistors 902 can have different resistance. The second path 906 of the bank of resistors 900 can include a plurality of switches 908 that can each be move to an open position or to a closed position. The first and second paths 904, 906 can be coupled via a plurality of links 910. Via the selective opening and/or closing of one or several of the switches 908 a current path can be created that can include all or portions of one or both of the first path 904 and the second path 906. In some embodiments, for example, the opening of a switch 908 can cause current to flow through a resistor 902 associated with that switch 908. Thus, in some embodiments, opening switch 908-A can create a current path through resistor 908-A, and closing of switch 908-B can create a current path around resistor 908-B, although some amount of current may still flow through resistor 908-B. Thus, the opening and closing of switches 908 can control the resistance of the adjustable resistance element 900. In some embodiments, the adjustable resistance element 806, and specifically, the opening and/or close of one or several of the switches 908 can be controlled by a processor of the IPG 10 such as, for example, the stimulation controller 702 of the pulse control 604.

The first circuit 802 can further comprise a first switch 812 and a second switch 814. The first switch 812 can be coupled to the first terminal 808 of the adjustable resistance element 806, and the first switch 812 can selectively couple the first terminal 808 of the adjustable resistance element 806 to one of a voltage node 816 and a ground node 818. In the embodiment shown in FIG. 8, the first switch 812 is in an open position. In some embodiments, the voltage node 816, also referred to herein as a stimulation-voltage node 816 can have a voltage controlled by, for example, the stimulation controller 702 of the pulse control 604.

The first circuit 802 further includes the second switch 814, which can selectively couple at least one of the electrodes 40, either directly, or indirectly such as via one of the switch arrays 710, 712, to the first circuit 802, and specifically to one: of the second terminal 810 of the adjustable resistance element 806; or a voltage node 816, which can, in some embodiments, be the same voltage node 816 to which the first switch 812 can couple. In some embodiments, the voltage node 816 to which the first switch 812 and the second switch 814 couple can be the same in that the voltage of both locations of coupling are the same and/or are controlled by a single voltage source and/or current source, thus, these nodes can have a common voltage. In the embodiment depicted in FIG. 8, the second switch 814 is shown in an open position. In some embodiments, the position of one or both of the first switch 812 and the second switch 814 can be controlled by a processor of the IPG 10 such as, for example, the stimulation controller 702 of the pulse control 604. In some embodiments, the first switch 812 and/or the second switch 814 can be controlled to generate all or portions of a stimulation pulse, which can be delivered to the tissue of the patient, which tissue can be tissue targeted for stimulation.

The first circuit 802 can further include a first capacitor 828 that can be located between the second switch 814 and the electrode 40. In some embodiments, and as depicted in FIG. 8, the first capacitor 828 can be part of the first circuit 802, and in some embodiments, the first capacitor 828 can be a part of the lead 20 and/or electrically coupled to the electrode 40.

The second circuit 804 can include an adjustable resistance element 818 having a first terminal 820 and a second terminal 822. The adjustable resistance element 818, also referred to herein as a second adjustable resistance element 818 can be controlled to have a desired resistance, and can be, in some embodiments, a variable resistor such as a potentiometer and/or a rheostat, or can be a digital resistor, and/or a bank of switchably connectable resistors. One embodiment of such a bank of switchably connectable resistors 900 is shown in FIG. 9 and is discussed above. In some embodiments, the adjustable resistance element 818, and specifically, the opening and/or close of one or several of the switches 908 can be controlled by a processor of the IPG 10 such as, for example, the stimulation controller 702 of the pulse control 604.

The second circuit 804 can further comprise a third switch 824 and a fourth switch 826. The third switch 824 can be coupled to the first terminal 820 of the adjustable resistance element 818, and the third switch 820 can selectively couple the first terminal 820 of the adjustable resistance element 818 to one of a voltage node 816 and a ground node 818. In the embodiment shown in FIG. 8, the third switch 824 is in an open position. In some embodiments, the voltage node 816 can have a voltage controlled by, for example, the stimulation controller 702 of the pulse control 604.

The second circuit 804 further includes the fourth switch 826, which can selectively couple at least one of the electrodes 40, either directly, or indirectly such as via one of the switch arrays 710, 712, to the second circuit 804, and specifically to one: of the second terminal 822 of the adjustable resistance element 818; or the voltage node 816. The voltage nodes 816 to which the switches 812, 814, 824, 826 can connect can have a common voltage, and thus can be common voltage nodes. In the embodiment depicted in FIG. 8, the fourth switch 826 is shown in an open position. In some embodiments, the position of one or both of the third switch 824 and the fourth switch 826 can be controlled by a processor of the IPG 10 such as, for example, the stimulation controller 702 of the pulse control 604. In some embodiments, the third switch 824 and/or the fourth switch 826 can be controlled to generate all or portions of a stimulation pulse, which can be delivered to the tissue of the patient, which tissue can be tissue targeted for stimulation.

The second circuit 804 can further include a second capacitor 830 that can be located between the fourth switch 826 and the electrode 40 coupled to the fourth switch 826. In some embodiments, and as depicted in FIG. 8, the second capacitor 830 can be part of the first circuit 802, and in some embodiments, the first capacitor 802 can be a part of the lead 20 and/or electrically coupled to the electrode 40.

In some embodiments, the position of one, some, or all of the switches 812, 814, 824, 826 can be controlled to selectively charge and/or discharge one or both of the capacitors 828, 830. Similarly, in some embodiments, the processor can adjust the resistance of one or both of the adjustable resistance elements 806, 818 to control a rate of at least one of the charging and the discharging of the at least one of the first and second capacitors 828, 830.

In some embodiments, the processor such as the stimulation controller 702 can control the switches, the voltage of the voltage node 816 and/or the resistance of one or both of the adjustable resistance elements 816, 818 to control a duration of the stimulation pulse, and/or an amplitude of the stimulation pulse. Thus, in some embodiments, the processor such as the stimulation controller 702 can control the stimulation circuitry 708 to deliver a stimulation pulse having a desired amplitude and/or duration.

In some embodiments, and as will be discussed in greater detail below, controlling the stimulation circuitry 708 to deliver a stimulation pulse having a desired amplitude and/or duration can include controlling the stimulation circuitry 708 to deliver a plurality of stimulation pulses with progressively increasing amplitudes until the stimulation pulse having the desired amplitude is delivered. Thus, in some embodiments, when a desired amplitude of a stimulation pulse is determined, the stimulation circuitry 708 can be iteratively controlled to increase amplitude of stimulation pulses until the desired stimulation pulse is achieved. In some embodiments, this iterative control can prevent the delivery of a stimulation pulse having a larger than desired current. In some embodiments, for example, impedance of target tissue can change as the stimulation current increases, and thus a step-wise method of increasing stimulation current, measuring impedance at the increased stimulation current, and delivering a new, increased stimulation current based on the measured impedance can prevent delivery of a larger than desired stimulation current.

The switches 812, 814, 824, 826 of the stimulation circuitry 708 can be controlled by a processor, and specifically by, in some embodiments, the stimulation controller 702 of the pulse control 604 to generate and/or deliver one or several stimulation pulses to the tissue of the patient. In some embodiments, this control of the switches 812, 814, 824, 826 can be phase-wise controlled such that some or all of the switches 812, 814, 824, 826 are arranged: in a first configuration for a first phase of delivery of a stimulation pulse; in an interphase configuration, also referred to as a second configuration or second switch configuration; in a third configuration for a second phase of delivery of the stimulation pulse; and in a neutral configuration upon completion of delivery of the stimulation pulse. In some embodiments, the interphase configuration can be the same as the neutral configuration.

The processor, such as the stimulation controller 702 can control the switches 812, 814, 824, 826 to create one or several switch configuration to thereby control and deliver a stimulation pulse. In some embodiments, for example, the switches can be in a neutral configuration, also referred to as an open configuration as shown in FIG. 8. In this configuration, no current is delivered to the target tissue and all of the switches 812, 814, 824, 826 are open. The switches 812, 814, 824, 826 can be in a first configuration for delivering of a first phase of a stimulation pulse.

Figure 10:
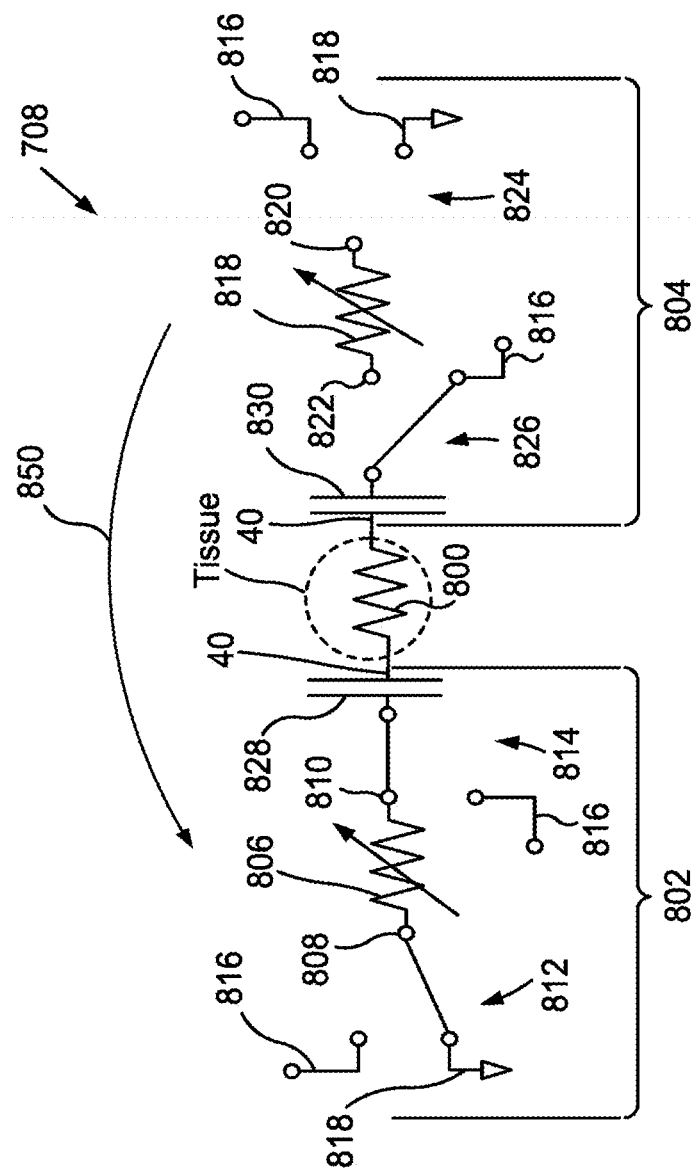
FIG. 10 is a schematic depiction of one embodiment of stimulation circuitry of an implantable pulse generator in a first configuration.

One embodiment of this first configuration is shown in FIG. 10. As seen in FIG. 10, the first switch 812 couples the first terminal 808 of the first adjustable resistance element 806 to the ground 818, the second switch 814 couples to the second terminal 810 of the adjustable resistance element 806, and the fourth switch 826 couples to the voltage node 816. In this configuration, current as represented by arrow 850 flows between the ground 818 and the voltage node 816 through the target tissue. In some embodiments, this current flow in the first phase can charge the capacitors 828, 830. The current flowing through the target tissue can be controlled by control of the voltage of the voltage node 816 and/or control of the resistance of the adjustable resistance element 806.

Figure 11:
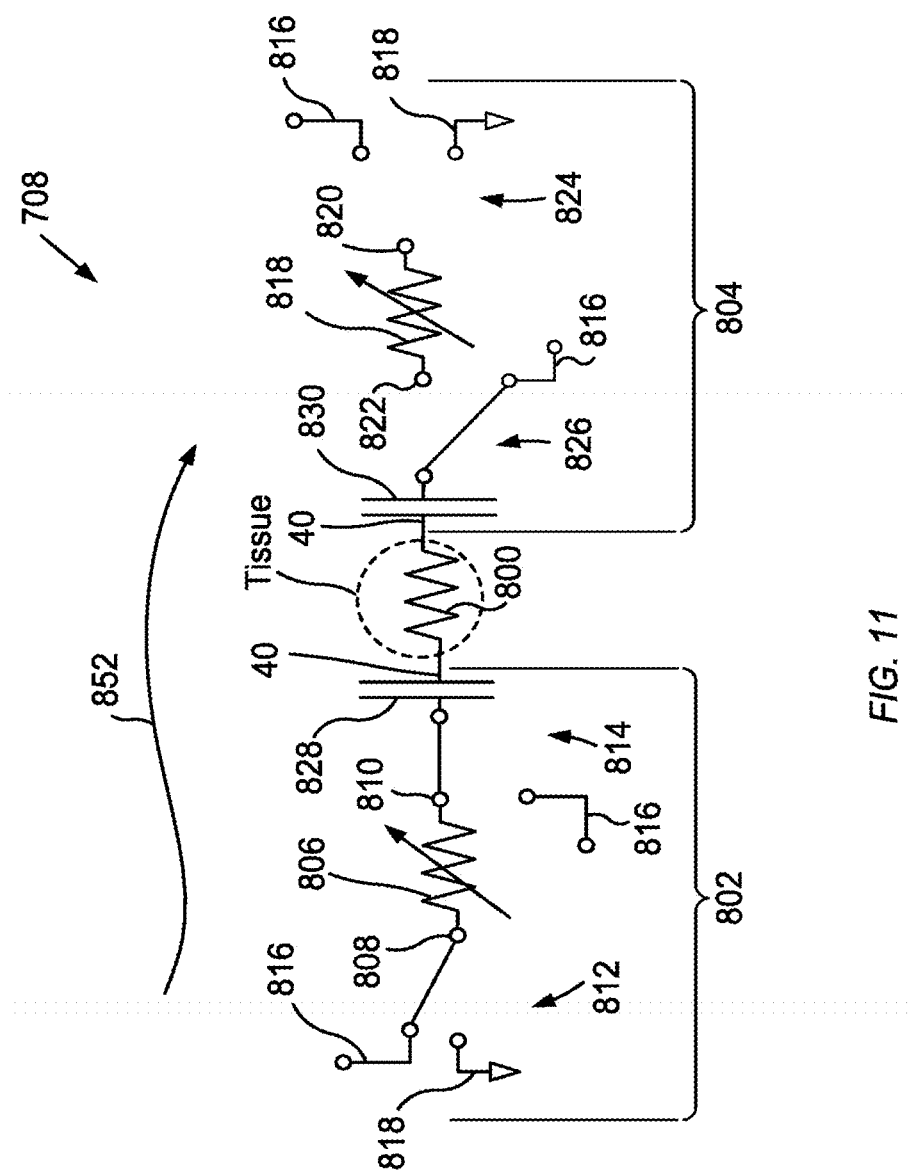
FIG. 11 is a schematic depiction of one embodiment of stimulation circuitry of an implantable pulse generator in a second configuration.

One embodiment of the second configuration is shown in FIG. 11. As seen in FIG. 11, the first switch 812 couples the first terminal 808 of the first adjustable resistance element 806 to the voltage node 816, the second switch 814 couples to the second terminal 810 of the adjustable resistance element, and the fourth switch 826 couples to the voltage node 816. The coupling of both the first circuit 802 and portions of the second circuit 804 to the voltage node 816 eliminates any voltage differential as the voltage node 816 to which the first circuit 802 and portions of the second circuit 804 is coupled is controlled to a single voltage. This elimination of any voltage differential allows the discharge of the capacitors 828, 830 creating a current, represented by arrow 852, flowing through the target tissue of the patient. This current flowing through the target tissue can be controlled by control of the resistance of the adjustable resistance element 806. In some embodiments, the charge of the capacitors can be known from information collected during the first phase, and, based on this charge information and the impedance of the target tissue, the resistance of the adjustable resistance element 806 can be set to achieve a desired current through the target tissue and/or to maintain a current below a desired level.

In some embodiments, the voltage of the voltage node 816 can be variable. In some embodiments, for example, the voltage of the voltage node 816 can be set to a first level during the first phase of the stimulation, and the voltage of the voltage node 816 can be set to a second level during the second phase of the stimulation. In some embodiments, the second level can be less than the first level.

As seen in FIGS. 10 and 11, in some embodiments, only portions of the second circuit 804 are used to create the stimulation pulse. In such embodiments, the remaining portions of the second circuit 804, and specifically, the adjustable resistance element 818 of the second circuit 804 can be coupled to an additional electrode 40 and can be used to deliver a stimulation pulse to other targeted tissue.

Figure 12:
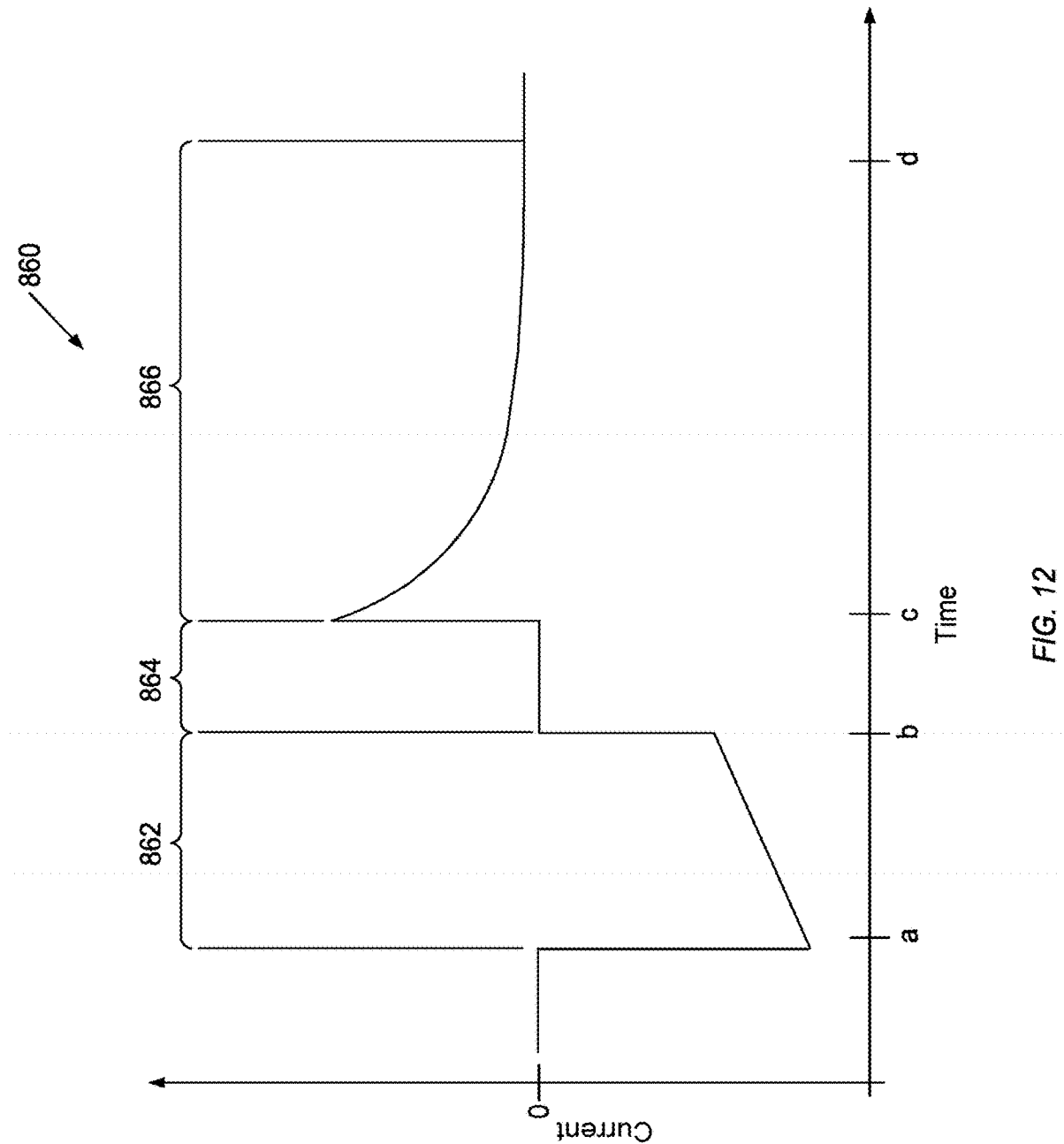
FIG. 12 is a graphical depiction of one embodiment of a stimulation pulse.

FIG. 12 shows a graphical depiction of a stimulation pulse 860. As depicted, the stimulation pulse starts at time "a" and extends through time "d." Prior to time "a", when the switches 812, 814, 824, 826 are in the neutral configuration, no current is flowing through the target tissue. At time "a", the first phase 862 starts via controlling some or all of switches 812, 814, 824, 826 to the first configuration, and terminates at time "b" via controlling some or all of switches 812, 814, 824, 826 to the interphase configuration, which in some embodiments is the neutral configuration. In some embodiments, impedance of the tissue of the patient can be measured shortly after the starting of the first phase 862. In such an embodiments, the voltage of the voltage node 816 can be combined with the current through the adjustable resistance element 806, which can be determined based on the resistance of the adjustable resistance element 806 and the voltage drop across the adjustable resistance element 806, to determine the impedance of the tissue of the patient. In some embodiments, this determination of the impedance of the patient's tissue can be made by the pulse control 604 and/or the stimulation controller 702.

In some embodiments, the transition to the neutral configuration can comprises the opening of at least one switch 812, 814, 824, 826. The interphase configuration creates the interphase delay 864 during which delay, in some embodiments, no current flows through the target tissue. The interphase delay 864 lasts until time "c", at which time the second phase 866 starts via controlling some or all of switches 812, 814, 824, 826 to the second configuration. In some embodiments, the transition The second phase 866 lasts until some or all of switches 812, 814, 824, 826 are controlled to transition to the third configuration, in which configuration current no longer flows through the target tissue. As seen in FIG. 12, the direction of current through the target tissue in the second phase 866 may be in the opposite direction of the current through the target tissue in the first phase 862. In some embodiments, the charge delivered during the second phase 866 is equal to the charge delivered during the first phase 862.

Figure 13:
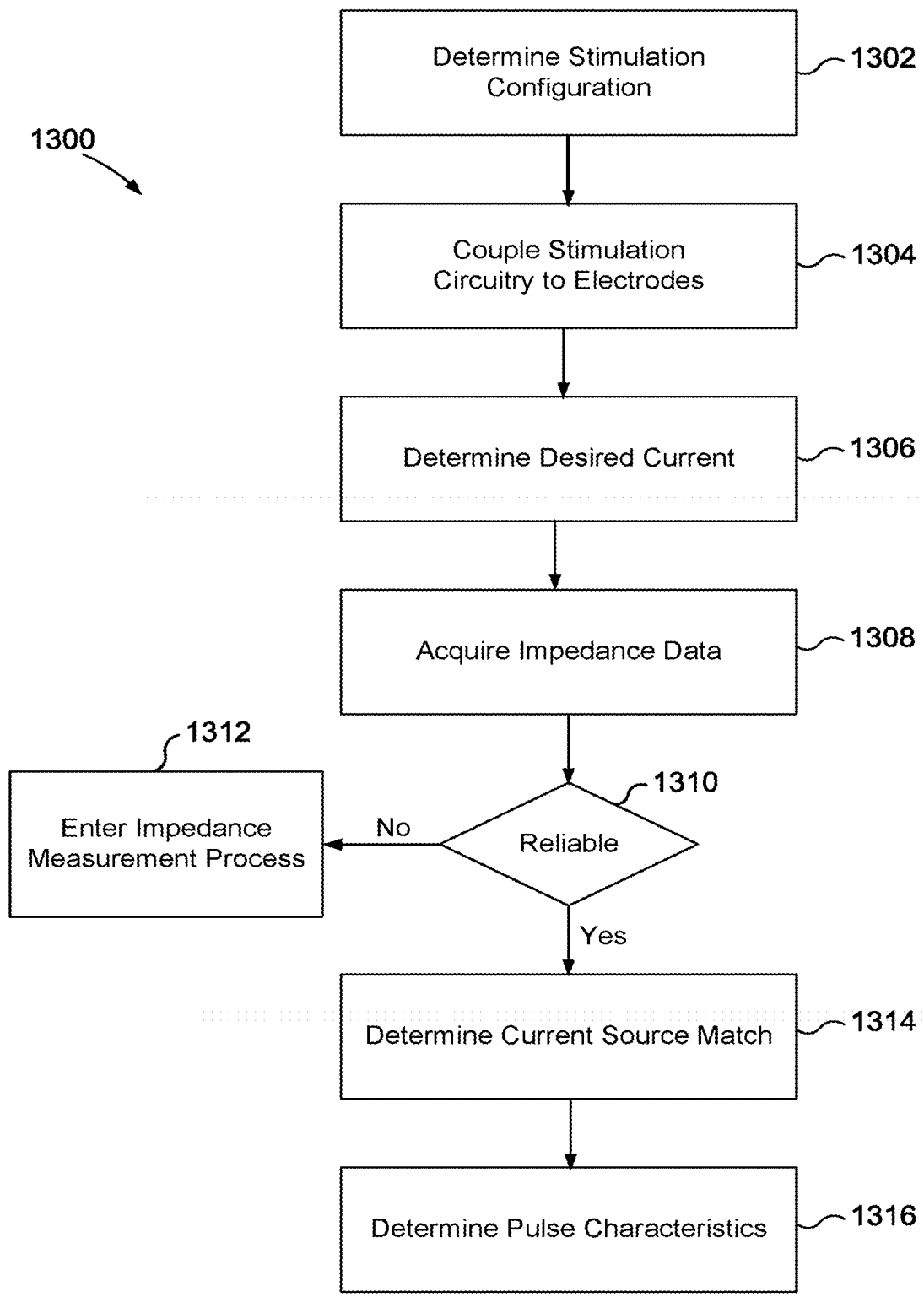
FIG. 13 is a flowchart depicting one embodiment of a first portion of a process for delivering stimulation and/or a stimulation pulse to target tissue of a patient.

FIG. 13 is a flowchart depicting one embodiment of a process 1300 for delivering stimulation and/or a stimulation pulse to target tissue of a patient. The process 1300 can be performed by the IPG 10 or by components or modules of the IPG 10 such as, for example, the pulse control 604. The process 1300 begins at block 1302, wherein a stimulation configuration is determined. In some embodiments, the determining of the stimulation configuration can include determining a desired coupling of one or several electrodes 40 of the lead 20 to the stimulation circuitry 708. This determining of the stimulation configuration can be performed by the pulse control 604. In some embodiments, this determining of the stimulation configuration can include the retrieving of information specifying the stimulation configuration from the memory of the IPG 10, which memory can be includes in the pulse control 604 and/or can be accessible by the pulse control 604.

After the stimulation configuration has been determined, the stimulation configuration can be implemented, as indicated in block 1304, by coupling stimulation circuitry to the electrodes 40. In some embodiments, this can be performed by the generation of one or several control signals by the stimulation controller 702, which control signals can control one or several switches of one or both of the switch arrays 710, 712. In some embodiments, this can include the coupling of all or portions of the first circuit 802 to a first electrode and coupling all or portions of the second circuit 804 to a second electrode.

At block 1306, a desired stimulation current is determined. In some embodiments, the determining of the desired stimulation current can be performed by the pulse control 604 and/or by the stimulation controller 702. In some embodiments, the determination of the desired stimulation current can include retrieving information specifying the desired stimulation current from the memory of the IPG 10. In some embodiments, the desired stimulation current can be determined based, at least in part, on one or several signals received from the patient remote.

At block 1308, impedance data for the target tissue to which the stimulation is to be delivered is acquired and/or determined. In some embodiments, the impedance of the target tissue can be measured and the acquiring of the impedance data can comprise the receipt of measurement data. In some embodiments, for example, the memory can contain previously measured impedance data for the target tissue and/or can include information specifying an impedance for use if the impedance of the target tissue has not been measured. In some embodiments, the impedance data may be associated with metadata identifying one or several attributes of the impedance data. This metadata can identify, for example, the age of the impedance data, the time/date of measuring of the impedance data, conditions under which the impedance data was gathered, or the like. In some embodiments, for example, the impedance of the target tissue may vary over time and/or may vary based on the current passed through the target tissue. In some embodiments, metadata associated with the impedance data can allow selection of impedance data most relevant to the desired current for a stimulation pulse. In some embodiments, for example, based on the desired current of the stimulation pulse, impedance data relevant to that desired current and/or most relevant to that desired current can be selected. In some embodiments, impedance data can be further selected based on the age of impedance data, specifically, the selection of impedance data can be according to function that diminishes the relevance of impedance data as the age of the impedance data increases.

At decision step 1310, it is determined if the impedance data from 1308 is reliable and/or sufficiently reliable for use. In some embodiments, for example, because of the age of the impedance data and/or because of the difference between the conditions under which the impedance data was gathered and current conditions, the impedance data may be identified as insufficiently reliable. In some embodiments, metadata associated with the impedance data may be compared to one or more thresholds delineating between reliable and unreliable data. If it is determined that the impedance data is unreliable, then the process 1300 proceeds to block 1312, wherein an impedance measuring process in entered and/or initiated.

If it is determined that the impedance data is reliable and/or is sufficiently reliable, then the process 1300 proceeds to block 1314 wherein a current source match is determined. In some embodiments, this can include determining one or several settings for use in controlling the current of the stimulation pulse and/or of one or more phases of the stimulation pulse. In some embodiments, this can include, for example, controlling the voltage of the voltage node 816 and/or the resistance of the adjustable resistance element 806 during the first phase of delivery of the stimulation pulse and controlling of the resistance of the adjustable resistance element 806 during the second phase of delivery of the stimulation pulse.

At block 1316, pulse characteristics of the stimulation pulse are determined. In some embodiments, this can include determining the duration of the stimulation pulse, determining the duration of one or several phases of the stimulation pulse, or the like. In some embodiments, the pulse characteristics of the stimulation pulse can be determined based on information retrieved from the memory of the IPG 10, the retrieved information specifying the characteristics of the stimulation pulse.

Figure 14:
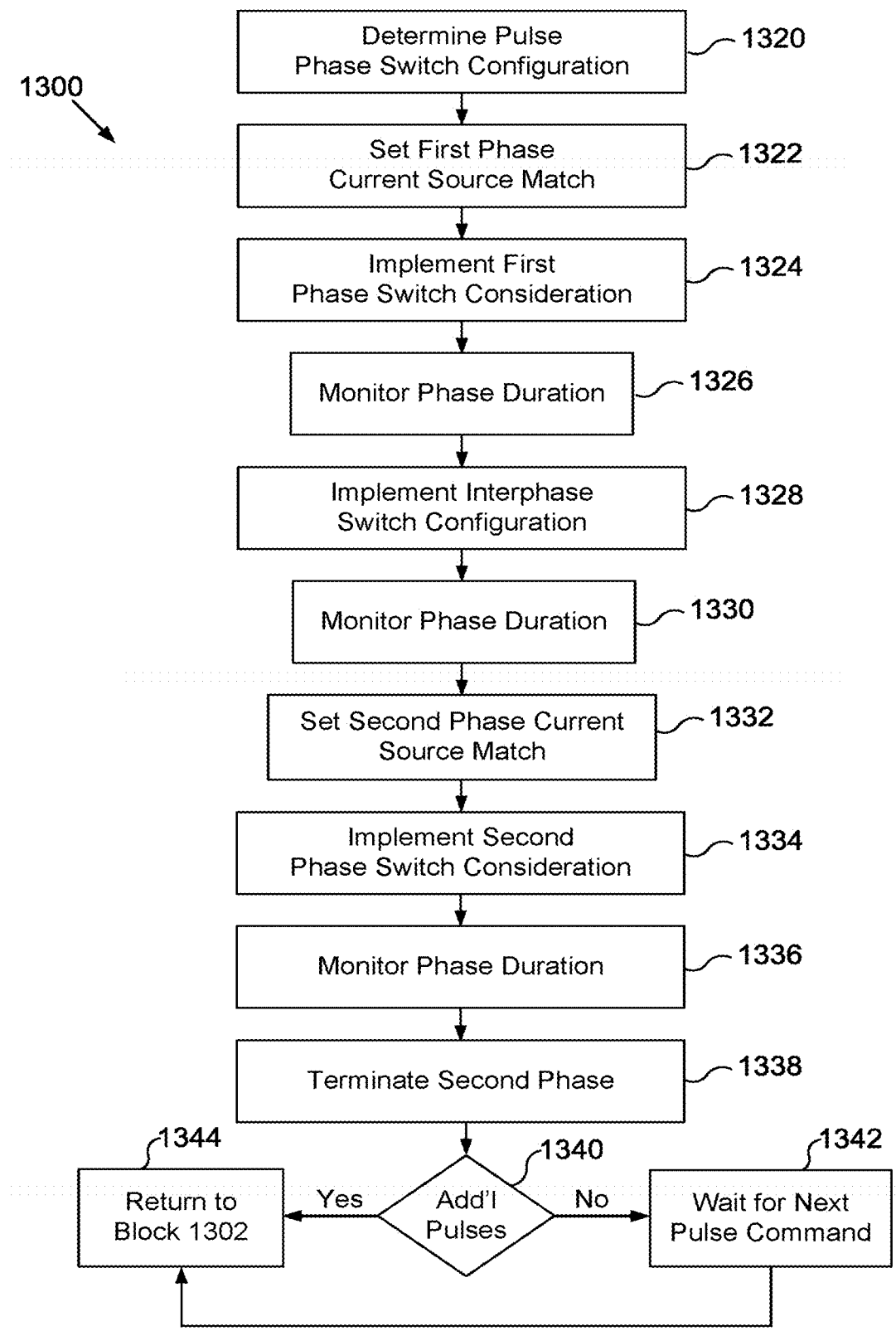
FIG. 14 is a flowchart depicting one embodiment of a second portion of the process for delivering stimulation and/or a stimulation pulse to target tissue of a patient.

At block 1320 shown in FIG. 14, one or several pulse switch configurations are determined. In some embodiments, this can include determining the phases for delivery of the stimulation pulse, and/or the duration of the phases for delivery of the stimulation pulse. In some embodiments, this determining of the switch configurations can be performed by the pulse control 604, and specifically by the stimulation controller 702. In some embodiments, determining of the one or several pulse phase configurations can include retrieving information specifying the one or several pulse phase configurations from the memory.

At block 1322, the first phase current source match is set. In some embodiments, this can include setting the voltage of the voltage node 816 and/or setting and/or adjusting the resistance of the adjustable resistance element 806. In some embodiments, the adjustable resistance element 806 can comprise a bank of switchably connected resistors, and adjusting the resistance of the adjustable resistance element can include changing a switch configuration of at least one of the plurality of resistors. The setting of the first phase current source match can be performed by the stimulation controller 702.

At block 1324, the first phase switch configuration is implemented and the first phase of the stimulation pulse is delivered via the implementing of the first switch configuration in the first circuit 802 and in the second circuit 804 of the stimulation circuitry 708. In some embodiments, this can include transitioning one or several of the switches 812, 814, 824, 826 of the first circuit 802 and/or the second circuit 804 from the neutral switch configuration to the first switch configuration. In some embodiments, the transitioning of the one or several switches 812, 814, 824, 826 can be simultaneously performed and/or the control signals for the transitioning of the switches 812, 814, 824, 826 can be simultaneously sent.

At block 1326, the duration of the first phase is monitored. In some embodiments, this can include triggering a timer tracking the duration of the first phase, triggering a count-down timer that expires at the time of desired termination of the first phase, or the like. In some embodiments, the pulse control 604 can include a timer and/or a count-down timer that can be used in determining the duration of the first phase.

At the termination of the first phase, in some embodiments, the interphase switch configuration can be implemented, via, for example, the generation and delivery of control signals directing the transitioning of the switches 812, 814, 824, 826 from the first configuration to the interphase switch configuration, the interphase switch configuration causing an interphase delay between the delivery of the first phase of the stimulation pulse and the second phase of the stimulation pulse. In some embodiments, this interphase switch configuration is the second switch configuration in the process 1300. In some embodiments, the transitioning of the one or several switches 812, 814, 824, 826 can be simultaneously performed and/or the control signals for the transitioning of the switches 812, 814, 824, 826 can be simultaneously sent.

At block 1328, the duration of the second phase is monitored. In some embodiments, this can include triggering a timer tracking the duration of the interphase, triggering a count-down timer that expires at the time of desired termination of the interphase, or the like. In some embodiments, the pulse control 604 can include a timer and/or a count-down timer that can be used in determining the duration of the second phase.

At block 1332, the second phase current source match is set. In some embodiments, this can include setting and/or adjusting the resistance of the adjustable resistance element 806. In some embodiments, this resistance can be set and/or adjusted based on the measured and/or expected impedance of the target tissue, and the charge of the capacitors 828, 830. The setting of the first phase current source match can be performed by the stimulation controller 702.

At block 1334, the second phase switch configuration, which is the third switch configuration of process 1300, is implemented and the second phase of the stimulation pulse is delivered via the implementing of the third switch configuration in the first circuit 802 and/or in the second circuit 804 of the stimulation circuitry 708. In some embodiments, this can include transitioning one or several of the switches 812, 814, 824, 826 of the first circuit 802 and/or the second circuit 804 from the interphase switch configuration, which can be the neutral switch configuration to the third switch configuration. In some embodiments, the transitioning of the one or several switches 812, 814, 824, 826 can be simultaneously performed and/or the control signals for the transitioning of the switches 812, 814, 824, 826 can be simultaneously sent.

At block 1336, the duration of the second stimulation phase is monitored. In some embodiments, this can include triggering a timer tracking the duration of the second phase, triggering a count-down timer that expires at the time of desired termination of the second phase, or the like. In some embodiments, the pulse control 604 can include a timer and/or a count-down timer that can be used in determining the duration of the second phase. At block 1338, the second phase is terminated. In some embodiments, the second stimulation phase can last until a termination threshold is met. The termination threshold can be a duration of time, a current level, or the like. In some embodiments, for example, the second phase terminates when current through the target tissue drops below a predetermined value. The pulse control 604, and specifically the stimulation controller 702 can terminate the second phase via the reconfiguration of the switches 812, 814, 824, 826 to, for example, the neutral configuration.

At decision step 1340, it is determined if additional stimulation pulses are desired. In some embodiments, for example, stimulation delivery can include the delivery of a plurality of stimulation pulses. In some embodiments, the delivery of stimulation can be limited by a predetermined number of pulses, a predetermined amount of time, or the like. In some embodiments, the pulse control 604, and specifically the stimulation controller 702 can track the number of pulses delivered and/or the duration of time that stimulation has been provided and can determine if delivery of stimulation is terminated.

If it is determined that no additional pulses are to be delivered, the process 1300 proceeds to block 1342 and waits for receipt of the next pulse command. In some embodiments, receipt of a pulse command can result in the generation and/or delivery of a stimulation pulse. After a pulse command is received, or alternatively, returning to decision step 1340, if it is determined that additional pulses are to be provided, the process 1300 proceeds to block 1344 and returns to block 1302.

Figure 15:
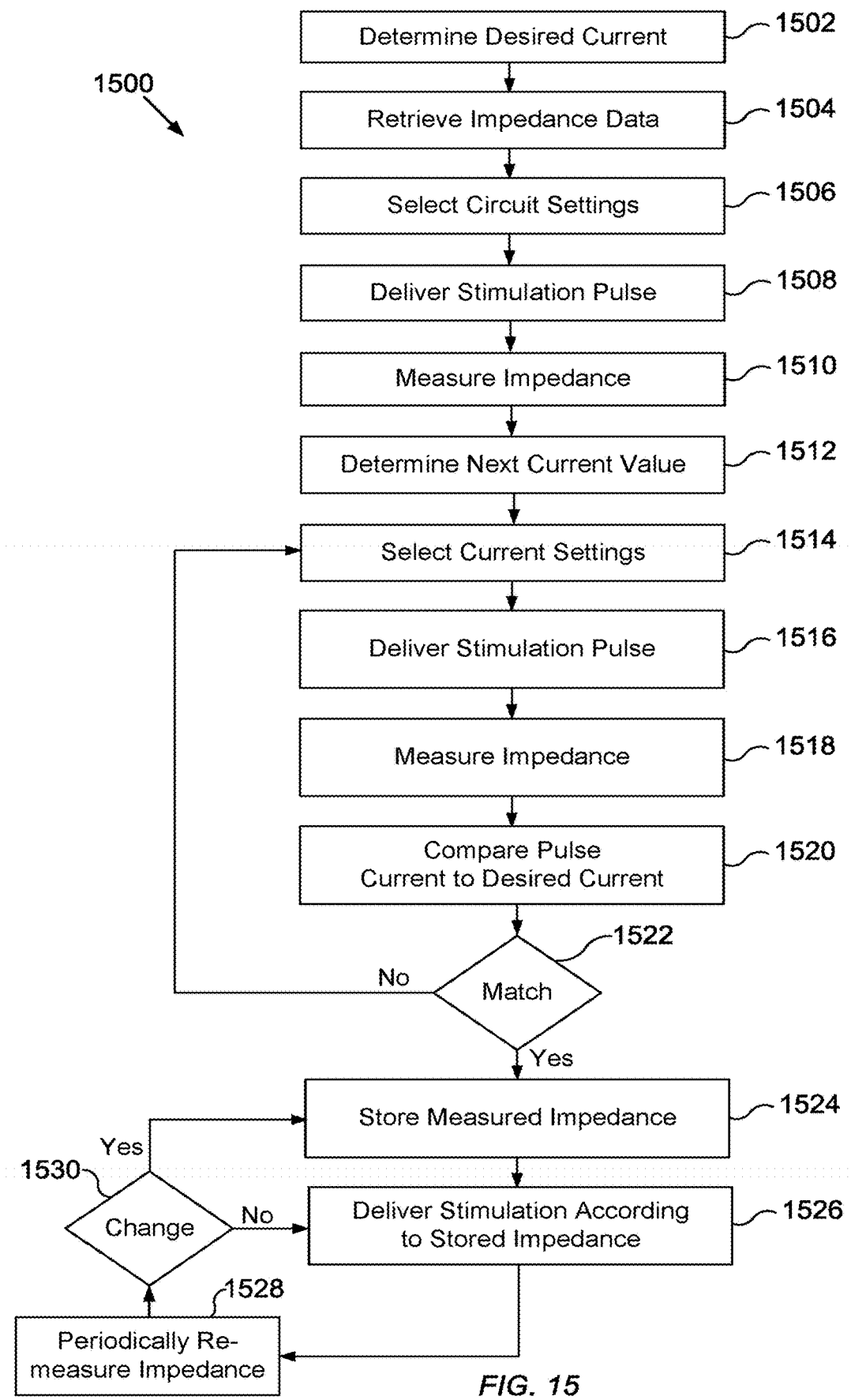
FIG. 15 is a flowchart depicting one embodiment of a process for delivering stimulation to a target tissue of a patient with an implantable pulse generator.

FIG. 15 depicts one embodiment of a process 1500 for delivering stimulation to a target tissue of a patient with an IPG 10. The process 1500 can be performed by the IPG 10 or by components or modules of the IPG 10 such as, for example, the pulse control 604. The process 1500 can be performed when impedance data is not sufficiently reliable. In some embodiments, the process 1500 can be performed when impedance data acquired in block 1308 of process 1300 is too old to be reliable, and/or is not applicable to one or several attributes of a desired stimulation, such as was measured at a different current than the desired stimulation. In some embodiments, the performing of process 1500 iteratively: increases a current of a delivered stimulation pulse and measures the impedance of the target tissue during the delivery of the stimulation pulse or determines the impedance of the target tissue based on data gathered during delivery of the stimulation pulse. This iterative approach allows the quick determination of tissue impedance at, or approximately at the desired current, and allows the IPG 10 to quickly deliver the desired stimulation current without exceeding, or significantly exceeding the desired current. In some embodiments, a desired current of a stimulation pulse is significantly exceeded when a patient experiences an adverse effect of the stimulation pulse.

The process begins at block 1502, wherein a desired current is determined. In some embodiments, the determining of the desired stimulation current can be performed by the pulse control 604 and/or by the stimulation controller 702. In some embodiments, the determination of the desired stimulation current can include retrieving information specifying the desired stimulation current from the memory of the IPG 10. In some embodiments, the desired stimulation current can be determined based, at least in part, on one or several signals received from the patient remote.

At block 1504, the impedance data for the targeted tissue is retrieved and/or acquired. In some embodiments, the impedance data for the target tissue to which the stimulation is to be delivered is retrieved and/or acquired from the memory of the IPG 10. At block 1506 the current source match is determined, or in other words, the settings of the stimulation circuitry are determined. In some embodiments, this can include determining a voltage of the voltage node 816 and/or a resistance of the adjustable resistance element 806. In some embodiments, the current source match is determined based on a combination of the desired current and the retrieved impedance data. In some embodiments, and to prevent the delivery of too much current to the target tissue, the current source match can be determined to deliver a current lower than the desired current. In some embodiments, the delivered current can be significantly lower than the desired current. In some embodiments, the delivered current can be less than 10% of the desired current, less than 25% of the desired current, less than 50% of the desired current, less than 75% of the desired current, and/or less than 80% of the desired current. In such embodiments, the current source match is determined based on the retrieved impedance data and a target value for the delivered current.

At block 1508 a stimulation pulse is delivered. In some embodiments, this stimulation pulse, which can be a test stimulation pulse, can be delivered according to steps 1320 through 1338 of process 1300. A test stimulation pulse can be a stimulation pulse delivered with circuit settings intended to create a current through the target tissue less than the desired current. In some embodiments, for example, the IPG 10 may immediately transition to a pulse with a desired current, and in some embodiments, the IPG 10 may transition to a pulse with a desired current via one or several test stimulation pulses, which can have a current less than the desired current. In some embodiments, and as tissue impedance may change with current, one or several test stimulation pulses can be delivered to measure tissue impedance and to facilitate the delivery of a stimulation pulse having, and in some embodiments, not exceeding, the desired current.

At block 1510 impedance in the target tissue is measured and/or determined. In some embodiments, the impedance in the target tissue can be measured during all or portions of the delivery of the stimulation pulse and/or can be determined based on data gathered during all or portions of the delivery of the stimulation pulse. In some embodiments, for example, current through the adjustable resistance element 806 can be measured during delivery of the all or portions of the stimulation pulse and/or the charger and/or change in charge in one or both of the capacitors 828, 830 can be measured during delivery of all or portions of the stimulation pulse. This gathered data can then be used to determine the impedance of the target tissue of the patient.

At block 1512, a next current value is determined. In some embodiments, this can include determining a target value for current of a next delivered stimulation pulse. This next current and/or the target value for current of the next delivered stimulation pulse can be greater than the previously delivered current and/or than the previous target value for current. In some embodiments, this next current, though larger than the previously delivered stimulation current, can still be less than the desired current, and in some embodiments, this next current can be equal to the desired current.

At block 1514, the current source match for the next stimulation pulse is determined, or in other words, the settings of the stimulation circuitry are determined. In some embodiments, this can include determining a voltage of the voltage node 816 and/or a resistance of the adjustable resistance element 806. In some embodiments, determination of the current source match for the next stimulation pulse can include, for example, controlling the voltage of the voltage node 816 and/or the resistance of the adjustable resistance element 806 during the first phase of delivery of the stimulation pulse and controlling of the resistance of the adjustable resistance element 806 during the second phase of delivery of the stimulation pulse. In some embodiments, the current source match can determined based on a combination of the desired current and the retrieved impedance data.

At block 1516, a stimulation pulse is delivered, which stimulation pulse can be a test stimulation pulse. In some embodiments, this stimulation pulse can be delivered according to steps 1320 through 1338 of process 1300. This stimulation pulse can have current that is greater than the current of the stimulation pulse delivered in block 1508 and/or that is less than the desired current determined in block 1502. At block 1518 impedance in the target tissue is measured and/or determined. In some embodiments, the impedance in the target tissue can be measured during all or portions of the delivery of the stimulation pulse and/or can be determined based on data gathered during all or portions of the delivery of the stimulation pulse. In some embodiments, for example, current through the adjustable resistance element 806 can be measured during delivery of the all or portions of the stimulation pulse and/or the charger and/or change in charge in one or both of the capacitors 828, 830 can be measured during delivery of all or portions of the stimulation pulse. This gathered data can then be used to determine the impedance of the target tissue of the patient.

At block 1520, the current of the stimulation pulse delivered in block 1516 is compared to the desired current of the stimulation pulse. In some embodiments, this comparison can include the comparing of the desired current to the current of one or both of: the first phase of the stimulation pulse; and the second phase of the stimulation pulse. At decision step 1522, it is determined if the current of the stimulation pulse delivered in block 1516 matches and/or approximately matches the desired current. In some embodiments, this can include determining whether one or several termination criteria for iteratively delivering a stimulation pulse and measuring impedance of the target tissue have been met. In some embodiments, the current of the test stimulation pulse approximately matches the desired value of the current of the desired stimulation pulse when at least one of: the first phase current; or the second phase current approximately matches the desired value of the current of the desired stimulation pulse. In some embodiments, at least one of: the first phase current; or the second phase current approximately matches the desired value of the current of the desired stimulation pulse when the current of the at least one of: the first phase current; or the second phase current is within predetermined range about the desired value of the current of the desired stimulation pulse. In some embodiments, for example, the delivered current approximately matches the desired current when the delivered current has a value between 80% and 120% of the desired current, between 90% and 110% of the desired current, between 95% and 105% of the desired current, between 98% and 102% of the desired current, is at least 80% of the desired current, is at least 90% of the desired current, is at least 95% of the desired current, is at least 98% of the desired current, or is any other or intermediate percent of the desired current or within any other or intermediate range about the desired current.

If it is determined that the delivered current does not match the desired current, then the process 1500 returns to block 1512 and proceeds as outlined above. In some embodiments, this can include delivering a third stimulation pulse having a third current, a fourth stimulation pulse having a fourth current, a fifth stimulation pulse having a fifth current, and/or any other number of stimulation pulses until one or several termination criteria are met and/or until a delivered current matches the desired current. In some embodiments, each subsequently delivered stimulation pulse can have a current greater than previously delivered stimulation pulses. Thus, in some embodiments, the third stimulation pulse can have a third current that is greater than the second current.

If it is determined that the delivered current matches the desired current, then the process 1500 proceeds to block 1524, wherein the measured impedance value is stored. In some embodiments, this impedance value can be stored in the memory of the IPG 10, and metadata associated with the impedance value can likewise be stored in the memory of the IPG 10.

At block 1526, stimulation is delivered according to the stored impedance value. In some embodiments, the delivery of stimulation can be according to the process 1300 of FIGS. 13 and 14. In some embodiments, the delivery of stimulation can comprise the delivery of a plurality of stimulation pulses. At block 1528, impedance of the target tissue is periodically re-measured. In some embodiments, this impedance of the target tissue can be re-measured at a predetermine time interval and/or after a predetermined number of delivered stimulation pulses. After the re-measuring of the impedance of the target tissue, the process 1500 can proceed to decision step 1530, wherein it is determined if there is a change in impedance of the target tissue. If it is determined that there is a change in the impedance of the target tissue, then the process 1500 proceeds to block 1524, and proceeds as outlined above. Alternatively, if it is determined that there is not a change in the impedance of the target tissue, then the process 1500 proceeds to block 1526 and proceeds as outlined above.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. An implantable neurostimulator for delivering one or more stimulation pulses to a target region within a patient's body, the implantable neurostimulator comprising:
   a housing;
   an energy storage feature located within the housing;
   at least one lead coupled to the housing and comprising a plurality of electrodes located proximate to a distal end of the at least one lead, wherein the energy storage feature is configured to provide power to produce a voltage at a stimulation voltage node; and
   a processor configured to control the operation of the neurostimulator,
   a stimulation circuitry comprising a first circuit configured to selectively couple the target region to the stimulation voltage node;
   wherein the first circuit comprises a first adjustable resistance element and a first capacitor between the adjustable resistance element and the target region;
   wherein the one or more stimulation pulses comprises a first stimulation phase and a second stimulation phase;
   wherein a voltage at the stimulation voltage node and a resistance of the first adjustable resistance element are both adjusted during the first stimulation phase by the processor to control a charge rate of the first capacitor, and wherein the resistance of the first adjustable element is further adjusted during the second phase to control the discharge rate of the first capacitor;

wherein the voltage at the stimulation voltage node and the resistance of the first adjustable resistance element are both adjusted based on a measurement of a value indicative of a tissue impedance of the target region to provide a desired value of a stimulation current for the one or more stimulation pulses;
wherein the first circuit further comprises:
a first switch configured to selectively couple the first adjustable resistance element between the stimulation voltage node and a ground node;
a second switch configured to selectively couple the first capacitor between the stimulation voltage node and the first adjustable resistance element;
a second circuit, wherein the second circuit comprises:
a second adjustable resistance element;
a second capacitor between the second adjustable resistance element and the target region;
a third switch configured to selectively couple the second adjustable resistance element between the stimulation voltage node and the ground node;
a fourth switch configured to selectively couple the second capacitor between the stimulation voltage node and the second adjustable resistance element;
wherein the stimulation circuitry is configured so that during the first stimulation phase, the first switch couples the first adjustable resistance element to the ground node and the fourth switch couples the second capacitor to the stimulation voltage node such that current travels from the stimulation voltage node at the second circuit to the ground node at the first circuit; and
wherein the stimulation circuitry is configured so that during the second stimulation phase, the first switch couples the first adjustable resistance element to the stimulation voltage node and the fourth switch couples the second capacitor to the stimulation voltage node so that the first circuit and second circuit is connected to the stimulation voltage node to eliminate voltage differential and to allow a discharge of the first and second capacitors and the flow of current from the first circuit to the target region then to the second circuit.

2. The implantable neurostimulator of claim 1, the voltage of the stimulation voltage node is set to a first voltage during the first phase and to a second voltage during the second phase.

3. The implantable neurostimulator of claim 1, further comprising an interphase delay between the first and second stimulation phase.

4. The implantable neurostimulator of claim 3, wherein the first, second, third, and fourth switch includes a neutral state to allow a pulse control module to control the first, second, third, and fourth switch to set the interphase delay.

5. The implantable neurostimulator of claim 1, wherein the first and second adjustable resistance element comprises at least one of a variable resistor, a digital resistor, and a bank of resistors switchably connectable to generate a desired combined resistance.

6. The implantable neurostimulator of claim 1, wherein the desired value of the stimulation current is adjusted repeatedly based on the measurement of the value indicative of the tissue impedance.

7. The implantable neurostimulator of claim 6, wherein the measurement of the value indicative of the tissue impedance is gathered during delivery of the one or more electrical pulses.

8. The implantable neurostimulator of claim 6, wherein the measurement of the value indicative of the tissue impedance is gathered after a predetermined number of stimulation pulses.

9. The implantable neurostimulator of claim 1, further comprising:
wherein the first circuit includes a first switch and a second switch;
wherein the first switch is configured to selectively couple the first adjustable resistance element between the stimulation voltage node or a ground node; and
wherein the second switch is configured to selectively couple a first electrode of the plurality of electrodes between the stimulation voltage node and the first adjustable resistance element.

10. The implantable neurostimulator of claim 6, further comprising
a pulse control module, wherein the pulse control module is configured to control the first adjustable resistance element and the voltage at the stimulation voltage node; and
wherein said pulse control module is configured to progressively increase a stimulation current from a value below a desired value of the stimulation current in order to compensate for the change of impedance of the target region as the stimulation current is increased and prevent delivery of a larger than desired stimulation current.

11. The implantable neurostimulator of claim 1, wherein the first adjustable resistance element comprises at least one of a variable resistor, a digital resistor, and a bank of resistors switchably connectable to generate a desired combined resistance.

12. An implantable neurostimulator for delivering one or more stimulation pulses to a target region within a patient's body, the implantable neurostimulator comprising:
a housing;
an energy storage feature located within the housing;
at least one lead coupled to the housing and comprising a plurality of electrodes located proximate to a distal end of the at least one lead, wherein the energy storage feature is configured to provide power to produce a voltage at a stimulation voltage node; and
a processor configured to control the operation of the neurostimulator;
a stimulation circuitry comprising a first circuit configured to selectively couple the target region to the stimulation voltage node;
wherein the first circuit comprises a first adjustable resistance element and a first capacitor between the adjustable resistance element and the target region;
wherein the one or more stimulation pulses comprises a first stimulation phase and a second stimulation phase;
wherein a voltage at the stimulation voltage node and a resistance of the first adjustable resistance element are both adjusted during the first stimulation phase by the processor to control a charge rate of the first capacitor, and wherein the resistance of the first adjustable element is further adjusted during the second phase to control the discharge rate of the first capacitor;
a pulse control module, configured to measure a value indicative of a tissue impedance of the target region;
wherein the value indicative of the tissue impedance of the patient is measured;
wherein the pulse control module is configured to repeatedly adjust the voltage at the stimulation voltage node and a resistance of the first adjustable resistance element based on the measured value indicative of the tissue impedance of the target region to provide a desired value of a stimulation current for the one or more stimulation pulses while reducing the energy drawn from the energy storage feature; and
wherein the first circuit further comprises:
- a first switch configured to selectively couple the first adjustable resistance element between the stimulation voltage node and a ground node;
- a second switch configured to selectively couple the first capacitor between the stimulation voltage node and the first adjustable resistance element;

a second circuit, wherein the second circuit comprises:
- a second adjustable resistance element;
- a second capacitor between the second adjustable resistance element and the target region;
- a third switch configured to selectively couple the second adjustable resistance element between the stimulation voltage node and the ground node;
- a fourth switch configured to selectively couple the second capacitor between the stimulation voltage node and the second adjustable resistance element;

wherein the stimulation circuitry is configured so that during the first stimulation phase, the first switch couples the first adjustable resistance element to the ground node and the fourth switch couples the second capacitor to the stimulation voltage node such that current travels from the stimulation voltage node at the second circuit to the ground node at the first circuit; and wherein the stimulation circuitry is configured so that during the second stimulation phase, the first switch couples the first adjustable resistance element to the stimulation voltage node and the fourth switch couples the second capacitor to the stimulation so that the first circuit and second circuit is connected to the stimulation voltage node to eliminate voltage differential and to allow the flow of current from the first circuit to the target region then to the second circuit due to a discharge of the first and second capacitors.

13. The implantable neurostimulator of claim 12, wherein the measurement of the value indicative of the tissue impedance is gathered during delivery of the one or more electrical pulses.

14. The implantable neurostimulator of claim 12, wherein the measurement of the value indicative of the tissue impedance is gathered after a predetermined number of stimulation pulses.

15. The implantable neurostimulator of claim 12,
wherein the pulse control module is configured to control the first adjustable resistance element and the voltage at the stimulation voltage node; and
wherein said pulse control module is configured to progressively increase a stimulation current from a value below a desired value of the stimulation current in order to compensate for the change of the value indicative of the tissue impedance as the stimulation current is increased and prevent delivery of a larger than desired stimulation current.

16. The implantable neurostimulator of claim 12, wherein the first adjustable resistance element comprises at least one of a variable resistor, a digital resistor, and a bank of resistors switchably connectable to generate a desired combined resistance.

* * * * *